(12) United States Patent
Sashidhara et al.

(10) Patent No.: US 8,815,940 B2
(45) Date of Patent: Aug. 26, 2014

(54) COUMARIN-CHALCONES AS ANTICANCER AGENTS

(75) Inventors: Koneni Venkata Sashidhara, Lucknow (IN); Abdhesh Kumar, Lucknow (IN); Manoj Kumar, Lucknow (IN); Jayanta Sarkar, Lucknow (IN); Sudhir Kumar Sinha, Lucknow (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 13/814,401

(22) PCT Filed: Aug. 5, 2011

(86) PCT No.: PCT/IN2011/000515
§ 371 (c)(1),
(2), (4) Date: Feb. 5, 2013

(87) PCT Pub. No.: WO2012/017454
PCT Pub. Date: Feb. 9, 2012

(65) Prior Publication Data
US 2013/0210909 A1    Aug. 15, 2013

(30) Foreign Application Priority Data
Aug. 5, 2010   (IN) .......................... 1843/DEL/2010

(51) Int. Cl.
*A61K 31/35*     (2006.01)
*C07D 311/02*    (2006.01)

(52) U.S. Cl.
USPC ........................... 514/456; 549/287; 514/685

(58) Field of Classification Search
USPC ................................. 514/456, 685; 549/287
See application file for complete search history.

(56) References Cited

U.S. PATENT DOCUMENTS 6,767,916 B2 *   7/2004   Bombardelli et al. ........ 514/337

FOREIGN PATENT DOCUMENTS

WO          01/17984 A1        3/2001

OTHER PUBLICATIONS

Sashidhara et al. CAS: 154: 45853, 2010.*
K. W. Merz et al., "Synthese von Furocumarinen, 4-Hydroxy-5-Methoxyisophthalaldehyd," Archiv Der Pharmazie Und Berichte der Deutschen Pharmazeutischen Besellschaft, No. 274, pp. 292-310, 1936.

* cited by examiner

*Primary Examiner* — Rei-tsang Shiao
(74) *Attorney, Agent, or Firm* — Blank Rome LLP

(57) ABSTRACT

The present invention relates to certain coumarin/chalcone compounds or a pharmaceutically acceptable salt thereof. The present invention particularly relates to the coumarin/chalcone compounds as anticancer agents useful for the treatment of cancer. The present invention also relates to the process of preparation of the said compounds.

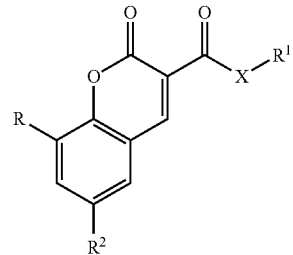

13 Claims, 3 Drawing Sheets

COUMARIN-CHALCONES AS ANTICANCER AGENTS

CROSS-REFERENCE TO RELATED APPLICATIONS

The present application is a National Phase of and claims the benefit of PCT/IN2011/000515, with an international filing date of Aug. 5, 2011, which in turn claims priority to Indian Application No. 1843/DEL/2010, filed Aug. 5, 2010, the entire disclosures of which are incorporated by reference herein.

FIELD OF THE INVENTION

The present invention relates to certain coumarin/chalcones and pharmaceutically acceptable salts thereof. The present invention particularly relates to the coumarin/chalcones as anticancer agents useful for the treatment of cancer. The present invention also relates to the process of preparation of the said compounds.

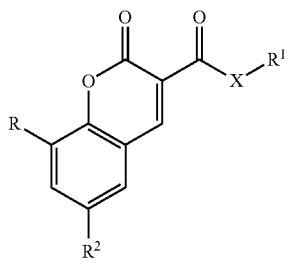

VI

R may be selected from the group consisting of:
H, CHO, COCH$_3$, NHCOCH$_3$, F, Cl, Br, NO$_2$, CF$_3$, OCF$_3$, CH$_3$, C$_2$H$_5$, C$_3$H$_7$, straight or branched alkyl chain up to six carbons, straight or branched alkoxy/sulphoxy chain up to six carbons, phenyl or substituted phenyl ring, wherein the substituents in phenyl ring are selected from a group consisting of F, Cl, Br, NO$_2$, CF$_3$, CH$_3$, C$_2$H$_5$, C$_3$H$_7$, and straight or branched alkyl chain up to six carbons.

X is selected from a group consisting of:
O, S, CH$_2$, NR$^3$, wherein R$^3$=H, CH$_3$, C$_2$H$_5$, C$_3$H$_7$ R$^1$ is selected from a group consisting of:
H, CH$_3$, C$_2$H$_5$, C$_3$H$_7$, straight or branched alkyl chain up to eight carbons, cyclopentyl, cyclohexyl, piperidinyl, unsubstituted or substituted phenyl ring, wherein the substituents in phenyl ring are selected from the group consisting of F, Cl, Br, NO$_2$, CF$_3$, CH$_3$, C$_2$H$_5$, OCH$_3$, OC$_2$H$_5$ and OCF$_3$.

R$^2$ is selected from a group consisting of:
CHO, —CH=CHCOR$^4$ wherein R$^4$ is selected from a group consisting of:
CH$_3$, C$_2$H$_5$, C$_3$H$_7$, straight or branched alkyl chain up to eight carbons, cyclopentyl, cyclohexyl, heteroaryl, piperidinyl, thienyl, furyl, pyridyl, indolyl and phenyl, which may be unsubstituted or substituted by one, two or three substituents being independently selected from a group consisting of F, Cl, Br, NO$_2$, CF$_3$, CH$_3$, C$_2$H$_5$, OCH$_3$, OC$_2$H$_5$, CF3, NMe$_2$, NEt$_2$, SCH$_3$, and NHCOCH$_3$.

wherein general formula VI is denoted by formula II where R$^2$=CHO; general formula VI is denoted by formula IV where R$^2$=—CH=CHCOR$^4$ and general formula VI is denoted by formula VII where X=NR$^3$ and R$^2$=—CH=CHCOR$^4$.

Also, the invention provides compounds of general formula III.

In a separate embodiment, the present invention provides a compound of general formula (III) or a pharmaceutically acceptable salt thereof

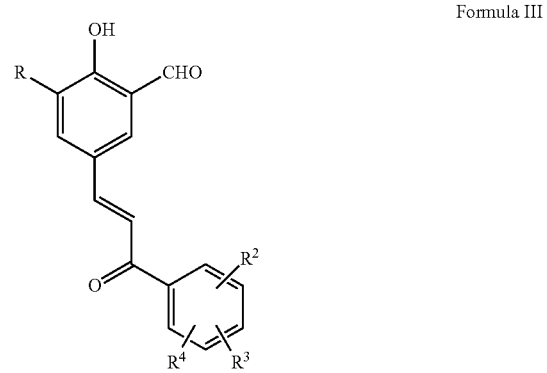

Formula III wherein:
R is selected from the group consisting of:
H, CHO, COCH$_3$, NHCOCH$_3$, F, Cl, Br, NO$_2$, CF$_3$, OCF$_3$, CH$_3$, C$_2$H$_5$, C$_3$H$_7$, straight or branched alkyl chain up to six carbons, straight or branched alkoxy/sulphoxy chain up to six carbons. unsubstituted or substituted phenyl ring, wherein the substituents in phenyl ring is selected from a group consisting of F, Cl, Br, NO$_2$, CF$_3$, CH$_3$, C$_2$H$_5$, OCH$_3$, OC$_2$H$_5$, and OCF$_3$.

R$^2$, R$^3$, R$^4$ which may be unsubstituted or substituted by one, two or three substituent's being independently selected from the group of consisting of F, Cl, Br, NO$_2$, CF$_3$, CH$_3$, C$_2$H$_5$, OCH$_3$, OC$_2$H$_5$, CF$_3$, NMe$_2$, NEt$_2$, SCH$_3$, and NHCOCH$_3$.

BACKGROUND OF THE INVENTION

Cancer, a diverse group of diseases characterized by uncontrolled growth of abnormal cells, is a major worldwide problem. It is a fatal disease standing next to the cardiovascular disease. Although the cancer research has led to a number of new and effective solutions. the medicines used as treatments have clear limitations and unfortunately cancer is projected as the primary cause of death in the future. Currently, there is a huge scientific and commercial interest in the discovery of potent, safe and selective anticancer drugs.

Cancer chemotherapy is the treatment that is performed that involves numerous agents such as docetaxel, vinorelbine, mitoxantrone and estramustine. These agents deactivate the cancer cells production. The general disadvantage of chemotherapy, no matter of type of cancer, is the drugs cannot discriminate between fast-growing cells and kills all cells whether they are part of controlled or uncontrolled process. Acting that way, chemotherapy kills and 'good cells', including hair follicles, causing typical side effects such as hair loss and other. Thus, the two most important defects of most contemporary anti-cancer agents are that 1. They exhibit poor selectivity toward cancer cells versus normal cells and
2. Poor efficacy against slow-growing tumors.

So there is need for new potent anticancer compounds that exhibit selectivity for cancerous cells over normal cells.

Accordingly, there is still a need in the art for potent cytotoxic agents for use in cancer therapy without having adverse effects on normal cells. Furthermore, there is also great need for additional anticancer agents that are easy to synthesis and are cost effective. Thus, one aim of the present invention is the provision of compounds which are potent anticancer agents that are non-toxic to normal cells and are easy to synthesize.

Natural as well as synthetic coumarins have recently drawn much attention due to its diverse pharmacological activities. Coumarin containing compounds have been demonstrated to have anticancer properties ((1) Kostova, I. Curr. Med. Chem. 2005, 5, 29. (2) Musa, M A.; Cooperwood, J. S. Curr. Med. Chem. 2008, 15, 2664). Recently, Lee et al. reported that Neo-Tanshinlactone, showed significant inhibition against two ER+ human breast cancer cell lines and was 10-fold more potent and 20-fold more selective as compared to Tamoxifen ((3) (a) Yizhou, D.; Quan, S.; Yi, N. L.; Xiang, W.; Kenneth. F. B.; Kuo, H. Lee. *J. Med. Chem.* 2009, 52, 3586. (b) Xihong, W.; Kyoko, N. G.; Kenneth, F. B.; Ming, J. D.; Yun, L. L.; Tian, S. W.; Kuo, H. Lee, *J. Med. Chem.* 2006, 49. 5631).

The recognition of key structural features within coumarin family is crucial for the design and development of new analogues with improved activity and for the characterization of their mechanism of action and potential side effects. The different substituent's in the coumarin nucleus strongly influence the biological activity of the resulting derivatives.

In continuation of our interest, in this class of compounds, ((4). (a) Sashidhara, K. V.; Kumar, A.; Kumar, M.; Sonkar, R; Bhatia, G.; Khanna, A. K. *Bioorg. Med. Chem. Lett.* 2010, 20, 4248. (b) Sashidhara, K. V.; Rosaiah, J. N.; Kumar, A.; Bhatia, G.; Khanna, A. K. *Bioorg. Med Chem. Lett.* 2010, 20, 3065. (c). Sashidhara, K. V., Kumar, A., Kumar, M., Srivastava, A., Puri, A. *Bioorg. Med. Chem. Lett.* 2010, 20 6504. (d) Sashidhara, K. V.; Rosaiah, J. N.; Bhatia, G.; Saxena, J. K. *Eur. J. Med. Chem.* 2008, 43, 2592) We embarked on the synthesis of novel coumarin derivatives as anticancer agents ((5). (a). Sashidhara, K. V., Kumar, A., Kumar, M., Sarkar, J., Sinha, S. *Bioorg. Med. Chem. Lett.* 2010, 20, 7205. (b) Sashidhara, K. V.; Rosaiah, J. N.; Kumar, M., Gara, R. K., Nayak, L. V., Srivastava, K., Bid, H. K., Konwar, R. *Bioorg. Med. Chem. Lett.* 2010, 20, 7127). Herein, we wish to describe the synthesis and biological evaluation of novel selective anticancer agents.

In the design of new drugs, the development of hybrid molecules through the combination of different pharmacophores may lead to compounds with interesting biological profiles. In recent years, combination chemotherapy with agents possessing different mechanisms of action is one of the methods that is being adopted to treat cancer. Therefore, a single molecule containing more than one pharmacophore, each with different mode of action could be beneficial for the treatment of cancer ((6). Mayur, Y. C.; Peters, G. J.; Prasad, V. V.; Lemo, C.; Sathish, N. K. *Curr. Cancer Drug Targets* 2009, 9, 298. (7). Solomon, V. R.; Hu, C.; Lee, H. *Bioorg. Med. Chem* 2009, 17, 7585). Adopting this approach, several research groups have recently reported hybrid molecules by coupling coumarins with different bioactive molecules.

The preparation and use of coumarin-resveratrol hybrids having the general formula shown in Formula A as antiplatelet agents are reported by (8) Vilar, S.; Quezada, E.; Santana, L.; Uriarte, E.; Yanez, M.; Fraiz, N.; Alcaide, C.; Cano, E.; Orallo, F. *Bioorg. Med. Chem. Lett.* 2006, 16, 257.

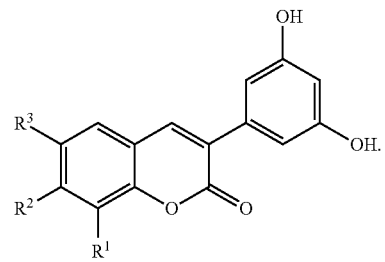

Formula A

The preparation and use of coumarin-maleimides hybrids having the general formula shown in Formula B as protein and antibody labelling agents are reported by (9) Song, H. Y.; Ngai, M. H.; Song, Z. Y.; MacAry, P. A.; Hobley, J.; Lear, M. J. *Org. Biomol. Chem.* 2009, 7, 3400.

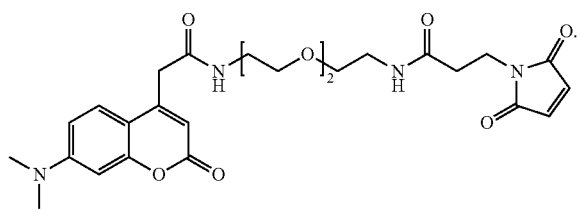

Formula B

The preparation and use of coumarin-lipoic acid conjugates having the general formula shown in Formula C as antioxidant and antiinflammatory agents are reported by (10). Melagraki, G.; Afantitis, A.; Igglessi, M. O.; Detsi, A.; Koufaki, M.; Kontogiorgis, C.; Hadjipavlou L. D. *Eur. J. Med. Chem.* 2009, 44, 3020.

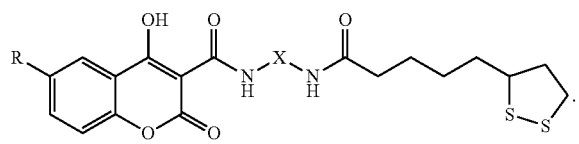

Formula C

The preparation and use of coumarin-stilbene hybrids having the general formula shown in Formula D as anticancer agents are reported by (11). Belluti, F.; Fontana, G.; Bo, L. D.; Carenini, N.; Giommarelli, C.; Zunino, F. *Bioorg. Med. Chem.* 2010, 18, 3543.

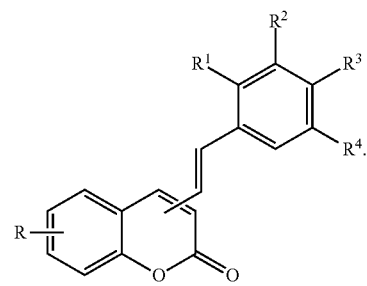

Formula D

Furthermore, preparation and use of coumarin-chalcone hybrids having the general formula shown in Formula E as anticancer agents are disclosed by (12). Bombardelli, E.; Valenti, P. WO 01/17984 A1, 2001 and U.S. Pat. No. 6,767, 916 B2.

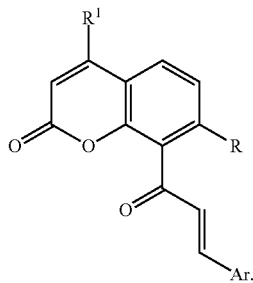

Formula E

But these compounds are not selective towards the cancer cell lines and also used in combination with other drugs. Keeping in mind these drawbacks, the Applicant has now synthesized highly selective coumarin/chalcone derivatives by a novel method, said derivatives are useful as anticancer agents. The anticancer selectivity of these novel compounds is due to appropriate positioning of the substituent, like the chalcone moiety at 6-position of benzocoumarin ring that enhances the activity and reduces toxicity. The compounds of this invention are a new structural class of coumarin chalcone that differ in significant ways from the previously known compounds. Representative examples of this invention are active as anti-tumor agents in mice bearing human tumor xenografts of cervical and prostate carcinoma, when dosed either intravenously or orally.

OBJECTIVES OF THE INVENTION

Main object of the present invention is to provide compounds of general formula III and VI or pharmaceutically acceptable salts thereof, which are useful as anticancer agents for the treatment or prevention of cervical carcinoma, oral squamous cell carcinoma or lung or prostate carcinoma or brain tumor.

Another objective of the invention is to provide a process of preparation of compounds of general formula III and VI or pharmaceutically acceptable salts thereof useful as anticancer agents for the treatment or prevention of cervical carcinoma, oral squamous cell carcinoma or lung or prostate carcinoma or brain tumor.

SUMMARY OF THE INVENTION

Accordingly, the present invention provides a compound of general formula (VI) or a pharmaceutically acceptable salt thereof,

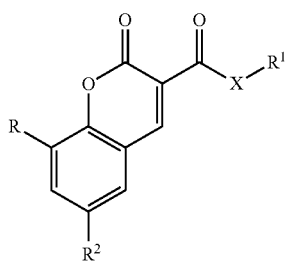

VI wherein:
R is selected from a group consisting of:
H, CHO, COCH$_3$, NHCOCH$_3$, F, Cl, Br, NO$_2$, CF$_3$, OCF$_3$, CH$_3$, C$_2$H$_5$, C$_3$H$_7$, straight or branched alkyl chain up to six carbons, straight or branched alkoxy/sulphoxy chain up to six carbons, phenyl or substituted phenyl ring, wherein the substituents in phenyl ring are selected from a group consisting of F, Cl, Br, NO$_2$, CF$_3$, CH$_3$, C$_2$H$_5$, C$_3$H$_7$, straight or branched alkyl chain up to six carbons,
X is selected from a group consisting of:
O, S, CH$_2$, NR$^3$, wherein R$^3$=H, CH$_3$, C$_2$H$_5$, C$_3$H$_7$.
R$^1$ is selected from a group consisting of:
H, CH$_3$, C$_2$H$_5$, C$_3$H$_7$, straight and branched alkyl chain up to eight carbons, cyclopentyl, cyclohexyl, piperidinyl, unsubstituted or substituted phenyl ring, wherein the substituents in phenyl ring are selected from the group consisting of F, Cl, Br, NO$_2$, CF$_3$, CH$_3$, C$_2$H$_5$, OCH$_3$, OC$_2$H$_5$, and OCF$_3$.
R$^2$ is selected from a group consisting of:
CHO, —CH=CHCOR$^4$
wherein R$^4$ is selected from a group consisting of:
CH$_3$, C$_2$H$_5$, C$_3$H$_7$, straight and branched alkyl chain up to eight carbons, cyclopentyl, cyclohexyl, heteroaryl, piperidinyl, thienyl, furyl, pyridyl, indolyl and phenyl, which may be unsubstituted or substituted by one, two or three substituents being independently selected from a group consisting of F, Cl, Br, NO$_2$, CF$_3$, CH$_3$, C$_2$H$_5$, OCH$_3$, OC$_2$H$_5$, CF3, NMe$_2$, NEt$_2$, SCH$_3$, and NHCOCH$_3$, wherein general formula VI is denoted by formula II where R$^2$=CHO; general formula VI is denoted by formula IV where R$^2$=—CH=CHCOR$^4$ and general formula VI is denoted by formula VII where X=NR$^3$ and R$^2$=—CH=CHCOR$^4$.

In one embodiment of the invention, the pharmaceutically acceptable salt is selected from a group consisting of solvates, amides, esters, ethers, chemically protected forms, and prodrugs of compound of formula VI.

In another embodiment of the invention, the compound of formula (VI) is useful as an anticancer agent for the treatment or prevention of cervical carcinoma, oral squamous cell carcinoma or lung or prostate carcinoma or brain tumor.

In another embodiment of the invention, the compound (VI) has a IC$_{50}$ value ranging between 1.53 to 146.82 µM.

Further embodiment of the invention discusses the representative compounds comprising:
I. Ethyl 8-sec-butyl-2-oxo-6-(3-oxo-3-p-tolylprop-1-enyl)-2H-chromene-3-carboxylate (S-009-0131)
II. Ethyl 8-sec-butyl-2-oxo-6-(3-oxo-3-phenylprop-1-enyl)-2H-chromene-3-carboxylate (S-009-0132)
III. Methyl 8-sec-butyl-2-oxo-6-(3-oxo-3-phenylprop-1-enyl)-2H-chromene-3-carboxylate (S-009-0133)
IV. Ethyl 8-sec-butyl-6-(3-(4-chlorophenyl)-3-oxoprop-1-enyl)-2-oxo-2H-chromene-3-carboxylate (S-009-0135)
V. Methyl 8-sec-butyl-6-(3-(4-chlorophenyl)-3-oxoprop-1-enyl)-2-oxo-2H-chromene-3-carboxylate (S-009-0136)
VI. (E)-8-tert-Butyl-N,N-diethyl-2-oxo-6-(3-oxo-3-p-tolylprop-1-enyl)-2H-chromene-3-carboxamide (S010-1992)
VII. (E)-8-sec-Butyl-N-methyl-2-oxo-6-(3-oxo-3-p-tolylprop-1-enyl)-2H-chromene-3-carboxamide (S010-1994)
VIII. (E)-8-sec-Butyl-N-ethyl-2-oxo-6-(3-oxo-3-p-tolylprop-1-enyl)-2H-chromene-3-carboxamide (S010-1995)

IX. (E)-8-sec-Butyl-N,N-diethyl-2-oxo-6-(3-oxo-3-p-tolylprop-1-enyl)-2H-chromene-3-carboxamide (S010-1996)
X. (E)-Ethyl 8-sec-butyl-2-oxo-6-(3-oxo-3-(3,4,5-trimethoxyphenyl)prop-1-enyl)-2H-chromene-3-carboxylate (S010-2000)
XI. (E)-Methyl 8-sec-butyl-2-oxo-6-(3-oxo-3-(3,4,5-trimethoxyphenyl)prop-1-enyl)-2H-chromene-3-carboxylate (S010-2001)
XII. (E)-Methyl 8-tert-butyl-2-oxo-6-(3-oxo-3-(3,4,5-trimethoxyphenyl)prop-1-enyl)-2H-chromene-3-carboxylate (S010-2003).
XIII. Ethyl 8-sec-butyl-6-formyl-2-oxo-2-H-chromene-3-carboxylate.

Another embodiment of the invention provides a process for preparation of general formula VI, comprising the steps of:

(a) reacting a compound of the formula (I) wherein R is selected from a group consisting of H, CHO, COCH$_3$, NHCOCH$_3$, F, Cl, Br, NO$_2$, CF$_3$, OCF$_3$, CH$_3$, C$_2$H$_5$, C$_3$H$_7$, straight or branched alkyl chain up to six carbons, straight or branched alkoxy/sulphoxy chain up to six carbons, phenyl or substituted phenyl ring, wherein the substituents in phenyl ring are selected from a group consisting of: F, Cl, Br, NO$_2$, CF$_3$, CH$_3$, C$_2$H$_5$, C$_3$H$_7$, and straight or branched alkyl chain up to six carbons, with an active methylene compound (in 1:1 to 1:1.2 w/w ratio) selected from diethylmalonate or dimethylmalonate, in an organic solvent in presence of a base at a temperature in the range between 40° C. to 120° C. for a period ranging between 1 to 8 hrs. removing the excess solvent under reduced pressure to obtain the residue, and neutralizing the residue with an acid to a pH 6.5-8.0, adding water and extracting the mixture with a water immiscible solvent selected from a group consisting of chloroform dichloromethane, ethyl acetate, diethyl ether, removing the solvent to dryness under reduced pressure and purifying the product by chromatographic methods to furnish compound of the formula (II), wherein R is selected form a group consisting of H, CHO, COCH$_3$, NHCOCH$_3$, F, Cl, Br, NO$_2$, CF$_3$, OCF$_3$, CH$_3$, C$_2$H$_5$, C$_3$H$_7$, straight or branched alkyl chain up to six carbons, straight or branched alkoxy/sulphoxy chain up to six carbons, phenyl or substituted phenyl ring, wherein the substituents in phenyl ring are selected from a group consisting of: F, Cl, Br, NO$_2$, CF$_3$, CH$_3$, C$_2$H$_5$, C$_3$H$_7$, and straight or branched alkyl chain up to six carbons and R$^1$ may be selected from the group of consisting of H, CH3, C2H5, C3H7, straight and branched alkyl chain up to eight carbons, cyclopentyl, cyclohexyl, piperidinyl, unsubstituted or substituted phenyl ring, wherein the substituents in phenyl ring are selected from the group consisting of F, Cl, Br, NO2, CF3, CH$_3$, C2H5, OCH3, OC2H5, and OCF3.

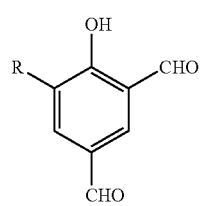

Formula I

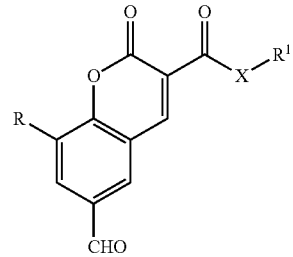

Formula II

Or (b) (i) reacting a compound of formula (I) wherein R is selected from a group consisting of H, CHO, COCH$_3$, NHCOCH$_3$, F, Cl, Br, NO$_2$, CF$_3$, OCF$_3$, CH$_3$, C$_2$H$_5$, C$_3$H$_7$, straight or branched alkyl chain up to six carbons, straight or branched alkoxy/sulphoxy chain up to six carbons, phenyl or substituted phenyl ring, wherein the substituents in phenyl ring are selected from a group consisting of: F, Cl, Br, NO$_2$, CF$_3$, CH$_3$, C$_2$H$_5$, C$_3$H$_7$, and straight or branched alkyl chain up to six carbons with a compound selected from a group consisting of acetophenone, p-methyl acetophenone, 3,4,5-trimethoxy acetophenone, p-trifluoromethyl acetophenone, m-methyl acetophenone, 4-methoxyphenyl acetophenone, 3-methylthio acetophenone, 4-chlorophenyl acetophenone, 2-chlorophenyl acetophenone, N-(4-acetylphenyl)acetamide, 1-(4-(diethylamino)phenyl)ethanone, 3,4-dimethoxyphenyl acetophenone, 3-fluorophenyl acetophenone, 3-bromophenyl acetophenone, 2-nitro acetophenone and 4-hydroxy acetophenone (in 1:1 to 1:1.5 w/w ratio) in presence of an acid or mild Lewis acid like iodine under neat reaction conditions or optionally in presence of an organic solvent at a temperature ranging between 40° C. to 120° C. for a period ranging between 1 to 7 hrs to give respective chalcone of the formula (III) wherein R is selected from a group consisting of H, CHO, COCH$_3$, NHCOCH$_3$, F, Cl, Br, NO$_2$, CF$_3$, OCF$_3$, CH$_3$, C$_2$H$_5$, C$_3$H$_7$, straight or branched alkyl chain up to six carbons, straight or branched alkoxy/sulphoxy chain up to six carbons, phenyl or substituted phenyl ring, wherein the substituents in phenyl ring are selected from a group consisting of: F, Cl, Br, NO$_2$, CF$_3$, CH$_3$, C$_2$H$_5$, C$_3$H$_7$, and straight or branched alkyl chain up to six carbons and R$^2$, R$^3$, R$^4$ which may be unsubstituted or substituted by one, two or three substituent's being independently selected from the group of consisting of F, Cl, Br, NO$_2$, CF$_3$, CH$_3$, C$_2$H$_5$, OCH$_3$, OC$_2$H$_5$, CF$_3$, NMe$_2$, NEt$_2$, SCH$_3$, and NHCOCH$_3$.

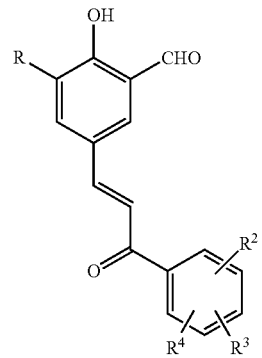

Formula III (ii) reacting a compound of the formula (III), with an active methylene compound selected from diethylmalonate or dimethylmalonate (in 1:1 to 1:1.2 w/w ratio), in an organic solvent in presence of a base at a temperature in the range between 40° C. to 120° C. for a period ranging between 1 to 8 hrs, removing the excess solvent under reduced pressure to obtain the residue, and neutralizing the residue with an acid, to a pH 6.5-8.0, adding water and extracting the mixture with a water immiscible solvent selected from a group consisting of chloroform, dichloromethane, ethyl acetate, diethyl ether, removing the solvent to dryness under reduced pressure and purifying the product by chromatographic methods to furnish compound of the formula (IV), wherein R is selected form a group consisting of H, CHO, COCH$_3$, NHCOCH$_3$, F, Cl, Br, NO$_2$, CF$_3$, OCF$_3$, CH$_3$, C$_2$H$_5$, C$_3$H$_7$, straight or branched alkyl chain up to six carbons, straight or branched alkoxy/sulphoxy chain up to six carbons, phenyl or substituted phenyl ring, wherein the substituents in phenyl ring are selected from a group consisting of: F, Cl, Br, NO$_2$, CF$_3$, CH$_3$, C$_2$H$_5$, C$_3$H$_7$, and straight or branched alkyl chain up to six carbons and R$^2$, R$^3$, R$^4$ which may be unsubstituted or substituted by one, two or three substituent's being independently selected from the group of consisting of F, Cl, Br, NO$_2$, CF$_3$, CH$_3$, C$_2$H$_5$, OCH$_3$, OC$_2$H$_5$, CF$_3$, NMe$_2$, NEt$_2$, SCH$_3$, and NHCOCH$_3$.

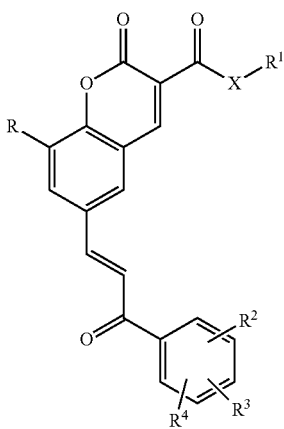

Formula IV (iii) adding aqueous KOH or NaOH (concentration ranging between 10% to 50%) solution to a solution of the compound of the formula (IV) in EtOH or MeOH and stirring the mixture vigorously for a period of between 1-4 hrs at a temperature between 15° C.-50° C., the solvents are removed and acidifying the residue with dilute HCl, adding water to the above residue and separating the precipitate to furnish crude product of the formula (V), R is selected form a group consisting of H, CHO, COCH$_3$, NHCOCH$_3$, F, Cl, Br, NO$_2$, CF$_3$, OCF$_3$, CH$_3$, C$_2$H$_5$, C$_3$H$_7$, straight or branched alkyl chain up to six carbons, straight or branched alkoxy/sulphoxy chain up to six carbons, phenyl or substituted phenyl ring, wherein the substituents in phenyl ring are selected from a group consisting of: F, Cl, Br, NO$_2$, CF$_3$, CH$_3$, C$_2$H$_5$, C$_3$H$_7$, and straight or branched alkyl chain up to six carbons and R$^2$, R$^3$, R$^4$ which may be unsubstituted or substituted by one, two or three substituents being independently selected from the group of consisting of F, Cl, Br, NO$_2$, CF$_3$, CH$_3$, C$_2$H$_5$, OCH$_3$, OC$_2$H$_5$, CF$_3$, NMe$_2$, NEt$_2$, SCH$_3$, and NHCOCH$_3$.

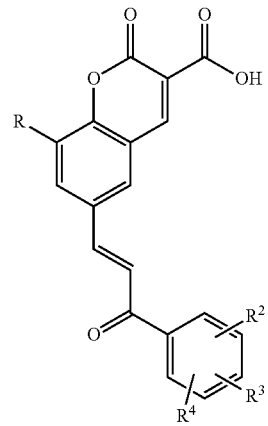

Formula V (iv) adding thionyl chloride to a compound of the formula (V) (in 2:1 to 2.5:1 w/w ratio) in an organic solvent selected from a group consisting of Dichloromethane (DCM), CCl$_4$, benzene, toluene and refluxed for a period ranging between 1-6 hrs, evaporating the resulting solution to dryness under reduced pressure, and dispersing the residue of crude product in an organic solvent selected from a group consisting of DCM, CCl$_4$, benzene, toluene, and further evaporating the solvent under reduced pressure obtain the residue and dissolving, it in a solvent selected from a group consisting of DCM, CCl$_4$, Benzene, Toluene and to obtain a solution, (v) adding an amine to the above solution obtained in step (iv) (in 1:1 to 1:1.5 w/w ratio) with stirring and allowing to react at temperature ranging between 15° C.-50° C. for a period ranging between 5-60 min, removing the solvent to dryness under reduced pressure and purifying the product by chromatographic methods to furnish the compound of formula (VII).

In yet another embodiment of the invention, the acid used in step (a) is selected from a group consisting of dilute HCl. dilute H$_2$SO$_4$, glacial acetic acid.

In yet another embodiment of the invention, the solvent used in step (a) is selected from a group consisting of dioxane, ethanol, THF, CCl$_4$ and benzene.

In another embodiment of the invention, the acid used in step (b) (i) and (ii) is selected from a group consisting of dilute HCl, dilute H$_2$SO$_4$, glacial acetic acid.

In another embodiment of the invention, wherein the solvent used in step (b) (i) and (ii) is selected from a group consisting of dioxane, ethanol, THF, benzene.

In yet another embodiment of the invention, the base used in step (b) (ii) is selected from a group consisting of pyridine, N-methyl morpholine, piperidine.

In still another embodiment of the invention, the amine used in step (b) (v) is selected from a group comprising of ethylamine, methylamine, N, N-diethylamine, N,N-dimethylamine, propylamine.

In a separate embodiment, the present invention provides a compound of general formula (III) or a pharmaceutically acceptable salt thereof Formula III

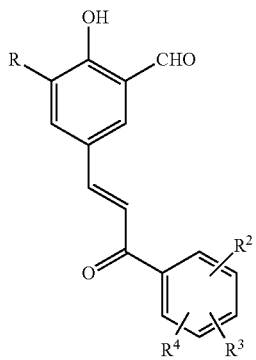

wherein:
R is selected from the group consisting of:
H, CHO, COCH$_3$, NHCOCH$_3$, F, Cl, Br, NO$_2$, CF$_3$, OCF$_3$, CH$_3$, C$_2$H$_5$, C$_3$H$_7$, straight or branched alkyl chain up to six carbons, straight or branched alkoxy/sulphoxy chain up to six carbons, unsubstituted or substituted phenyl ring, wherein the substituents in phenyl ring is selected from a group consisting of F, Cl, Br, NO$_2$, CF$_3$, CH$_3$, C$_2$H$_5$, OCH$_3$, OC$_2$H$_5$, and OCF$_3$.

R$^2$, R$^3$, R$^4$ which may be unsubstituted or substituted by one, two or three substituent's being independently selected from the group of consisting of F, Cl, Br, NO$_2$, CF$_3$, CH$_3$, C$_2$H$_5$, OCH$_3$, OC$_2$H$_5$, CF$_3$, NMe$_2$, NEt$_2$, SCH$_3$, and NHCOCH$_3$.

Yet another embodiment of the invention provides the compound of general formula (III). wherein the representative compounds comprising:

(I) (E)-3-sec-butyl-2-hydroxy-5-(3-oxo-3-p-tolylprop-1-enyl)benzaldehyde (S008-0392).
(II) (E)-3-tert-butyl-2-hydroxy-5-(3-oxo-3-p-tolylprop-1-enyl)benzaldehyde (S010-1985)
(III) (E)-3-sec-butyl-2-hydroxy-5-(3-oxo-3-(3,4,5-trimethoxyphenyl)prop-1-enyl)benzaldehyde (S010-1986)
(IV) (E)-3-sec-butyl-2-hydroxy-5-(3-oxo-3-(3,4,5-trimethoxyphenyl)prop-1-enyl)benzaldehyde (S010-1986)

The present invention also provides the use of a compounds of formula III and VI as anticancer agents. In particular, the compounds of the present invention are useful as an anticancer agent for the treatment or prevention of cervical carcinoma, oral squamous cell carcinoma or lung or prostate carcinoma or brain tumor.

In a separate embodiment of the invention, the present invention provides a pharmaceutical composition comprising of the general formula, (III) and/or (VI) as defined in preceding claims, in combination with one or more pharmaceutically acceptable salts optionally along with pharmaceutically acceptable excipients, diluents, binders, solvates, amides, esters, ethers, chemically protected forms, and prodrugs thereof.

The invention will now be described by way of illustrative examples (Scheme 1) and with reference to the accompanying formula drawings. The following examples are provided solely for the purpose of illustration and should not be construed so as to limit the scope of the invention.

DETAILED DESCRIPTION OF THE INVENTION COMPOUNDS

Example-1

Figure 1:
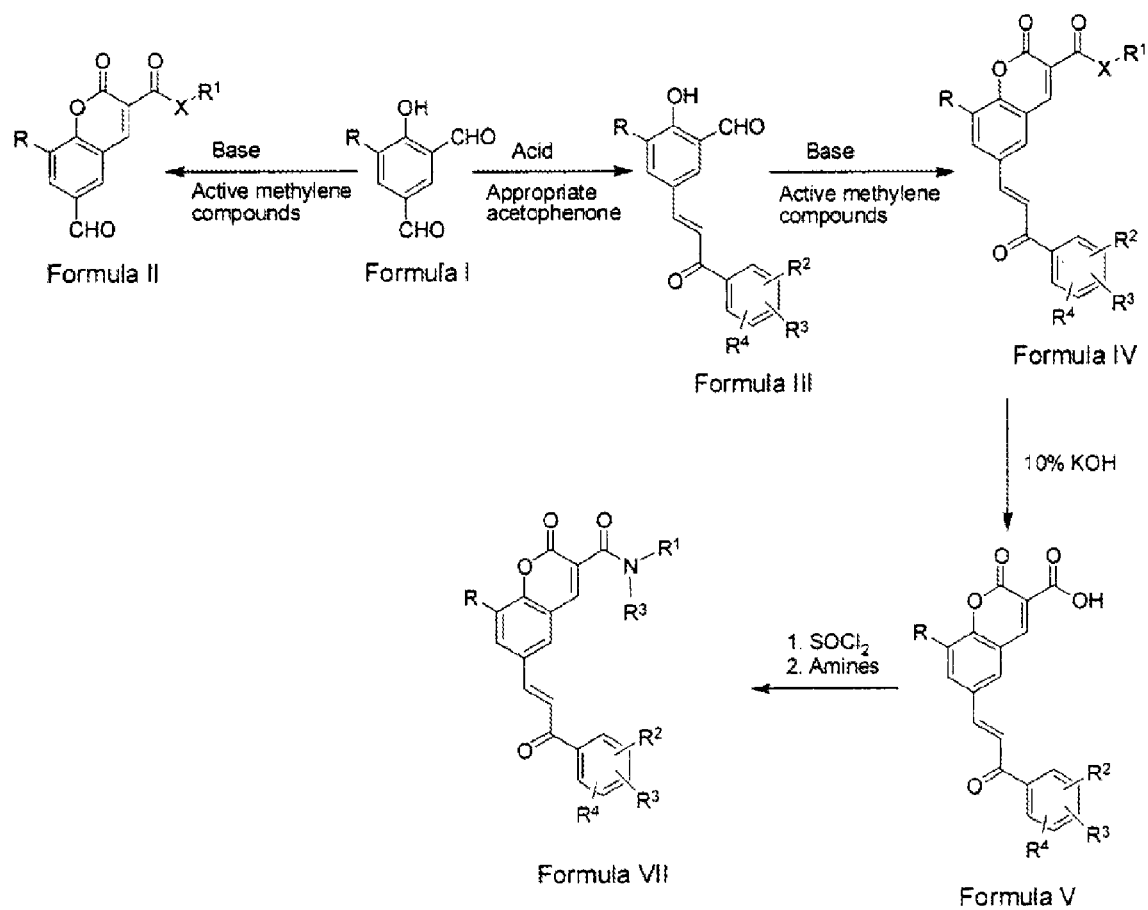
FIG. 1. General method for preparation of coumarin/chalcones.
Figure 2:
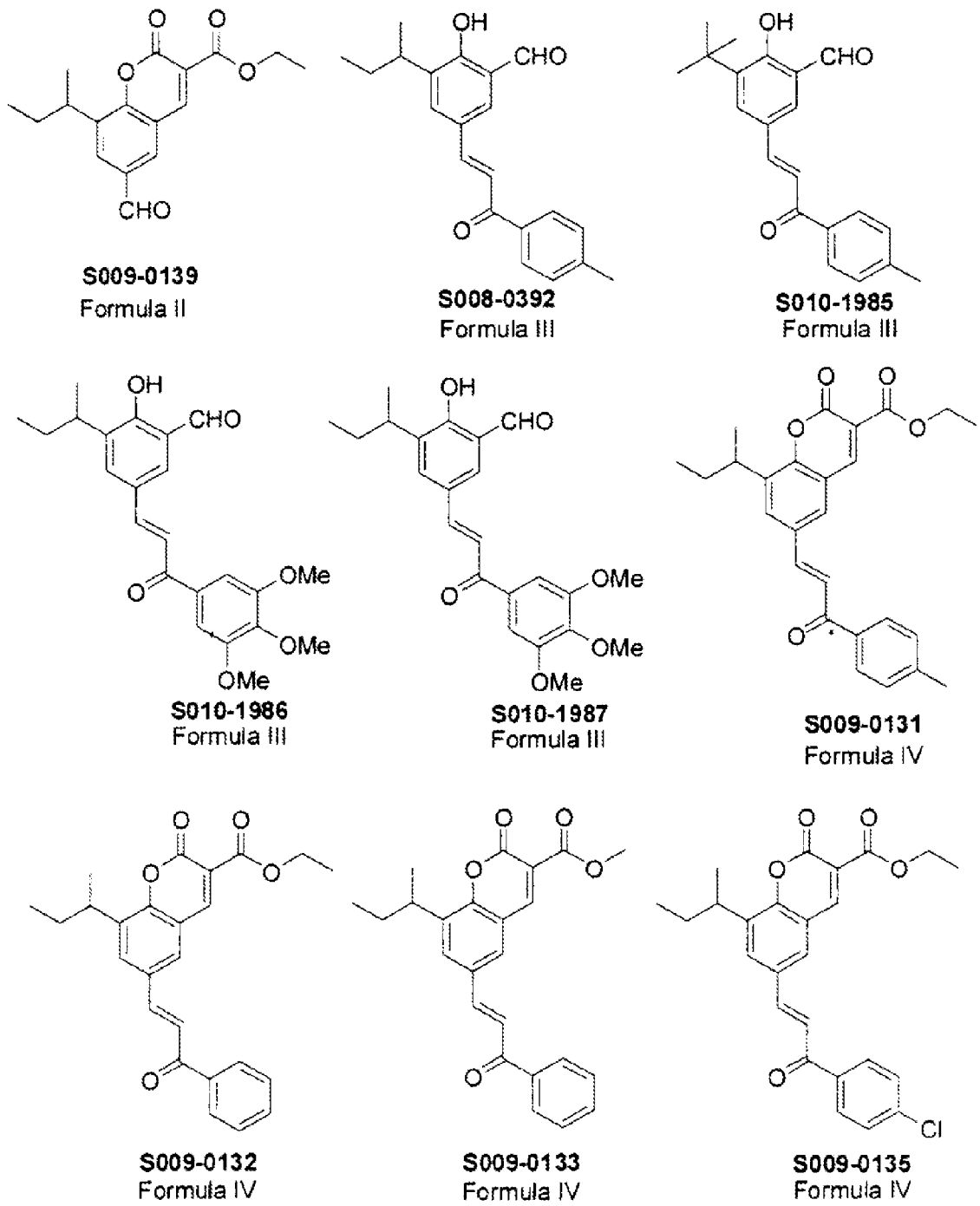
FIG. 2: Chemical structures of some representative examples of this invention.
Figure 2:
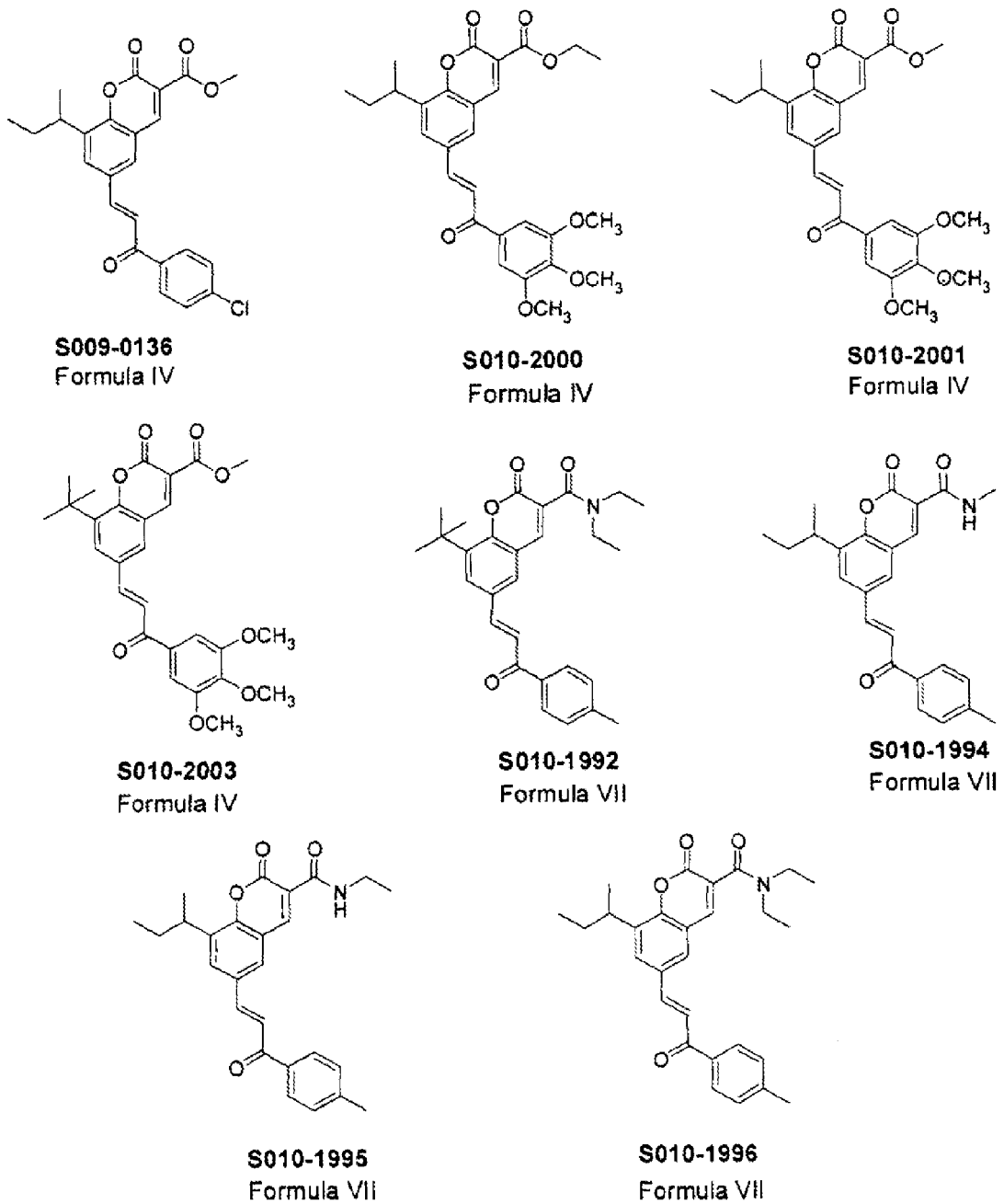

(E)-3-sec-butyl-2-hydroxy-5-(3-oxo-3-p-tolylprop-1-enyl)benzaldehyde (See Accompanying Formula Drawing S008-0392) (General Formula III)

A solution of 5-sec-butyl-4-hydroxyisophthalaldehyde of formula I (0.50 g, 3.05 mmol) and p-methyl acetophenone (0.41 g, 3.05 mmol) in dioxane (25 mL) was treated with conc.HCl (0.5 mL). The solution was heated at 80° C. for 2.5 h. Further, 0.5 mL of conc.HCl was added and reaction was continued for 2.5 h more. Most of the excess reagent was evaporated under reduced pressure, and the residue was suspended in water (50 mL) and extracted 3-fold with CHCl$_3$ (50 mL). The combined organic layers were dried on Na$_2$SO$_4$, filtered, and concentrated to dryness under reduced pressure. The residue was chromatographed over silica gel (SiO$_2$, 230-400 flash), eluting with a gradient of 4% ethyl acetate in hexane, which upon concentration provides (E)-3-sec-butyl-2-hydroxy-5-(3-oxo-3-p-tolylprop-1-enyl)benzaldehyde (General Formula III).

$^1$H NMR (CDCl$_3$, 200 MHz): δ 11.60 (s, 1H), 9.94 (s, 1H), 7.94 (d, J=8.0 Hz, 2H), 7.77 (d, J=15.7 Hz, 1H), 7.69 (d, J=2.4 Hz, 1H), 7.45 (d, J=15.7 Hz, 1H), 7.31 (d, J=8.1 Hz, 2H), 3.26-3.08 (m, 1H), 2.43 (s, 3H), 1.77-1.59 (m, 2H), 1.28 (d, J=6.6 Hz, 3H), 0.88 (t, J=8.0 Hz, 3H); $^{13}$C NMR (75 MHz): δ 196.8, 189.9, 161.5, 143.8, 143.3, 137.3, 135.8, 133.8, 132.1, 129.5, 128.8, 127.0, 120.9, 120.4, 33.5, 29.5, 21.8, 20.2, 12.2; ESI-MS (m/z): 323 (M+H)$^+$;

Example-2

(E)-3-tert-butyl-2-hydroxy-5-(3-oxo-3-p-tolylprop-1-enyl)benzaldehyde (See Accompanying Formula Drawing S010-1985) (General Formula III)

A solution of 5-tert-butyl-4-hydroxyisophthalaldehyde of formula I (0.50 g, 3.05 mmol) and p-methyl acetophenone (0.41 g, 3.05 mmol) in dioxane (25 mL) was treated with iodine (0.78 g, 0.31 mmol). The solution was heated at 90° C. for 5.0 h. Most of the excess reagent was evaporated under reduced pressure, and the residue was treated with aq. Na$_2$S$_2$O$_3$ solution (5%, 40 mL) and the product was extracted 3-fold with CHCl$_3$ (50 mL). The combined organic layers were dried on Na$_2$SO$_4$, filtered, and concentrated to dryness under reduced pressure. The residue was chromatographed over silica gel (SiO$_2$, 230-400 flash), eluting with a gradient of 4% ethyl acetate in hexane, which upon concentration provides (E)-3-tort-butyl-2-hydroxy-5-(3-oxo-3-p-tolyl-prop-1-enyl)benzaldehyde (General Formula III).

$^1$H NMR (CDCl$_3$, 300 MHz): δ 12.50 (s, 1H), 9.91 (s, 1H), 7.92 (d, J=8.2 Hz, 2H), 7.79-7.73 (m, 2H), 7.67 (d, J=2.0 Hz, 1H), 7.43 (d, J=15.6 Hz, 1H), 7.28 (d, J=8.0 Hz, 2H), 2.42 (s, 3H), 1.45 (s, 9H); $^{13}$C NMR (75 MHz): δ 197.0, 189.7, 162.9, 143.7, 143.3, 139.3, 135.7, 133.6, 132.5, 129.4, 128.7, 126.4, 120.7, 120.6, 35.0, 29.2, 21.7; ESI-MS (m/z): 323 (M+H)$^+$;

Example-3

Ethyl 8-sec-butyl-6-formyl-2-oxo-2H-chromene-3-carboxylate (See Accompanying Formula Drawing S009-0139) (General Formula II)

A solution of 5-sec-butyl-4-hydroxyisophthalaldehyde of formula I (0.5 g, 2.42 mmol), diethyl malonate (0.38 g, 2.42 mmol) in ethanol (20 mL) was treated with piperidine (0.3 mL) and refluxed. Most of the excess solvent was evaporated under reduced pressure, and the residue was neutralized with acetic acid. To this residue water (20 mL) was added and extracted 3-fold with 20 mL of $CHCl_3$. The combined organic layers were dried on $Na_2SO_4$, filtered, and concentrated to dryness under reduced pressure. The residue was chromatographed over silica gel ($SiO_2$, 230-400 flash), eluting with a gradient of 20% ethyl acetate in hexane to 40% ethyl acetate in hexane, which upon concentration provides ethyl 8-sec-butyl-6-formyl-2-oxo-2H-chromene-3-carboxylate (General Formula II). (0.47 g, 65% yield). White solid, m. p. 89-90° C.; $^1$H NMR ($CDCl_3$, 300 MHz): δ 10.05 (s, 1H), 8.60 (s, 1H), 8.05 (brs, 1H), 8.01 (brs, 1H) 4.44 (q, 2H, J=7.1 Hz), 3.51-3.40 (m, 1H), 1.78-1.69 (m, 2H), 1.43 (t, 3H, J=7.1 Hz), 1.33 (d, 3H, J=7 Hz), 0.88 (t, 3H, J=7.4 Hz); $^{13}$C NMR ($CDCl_3$, 75 MHz): δ 190.2, 162.7, 156.5, 155.8, 148.5, 137.3, 132.9, 131.7, 129.9, 119.2, 118.0, 62.2, 33.4, 29.6, 20.4, 14.2, 12.0; ESI-MS (m/z): 303 (M+H)$^+$.

Example-4

Methyl 8-sec-butyl-6-(3-(4-chlorophenyl)-3-oxo-prop-1-enyl)-2-oxo-2H-chromene-3-carboxylate (General Formula IV) See Accompanying Formula Drawing S009-0136)

A solution of 3-sec-butyl-5-(3-(4-chlorophenyl)-3-oxoprop-1-enyl)-2-hydroxybenzaldehyde of formula III (0.5 g, 1.46 mmol), dimethyl malonate (0.19 g, 1.46 mmol) in methanol (30 mL) was treated with N-methyl morpholine (0.3 mL) and refluxed. Most of the excess solvent was evaporated under reduced pressure, and the residue was neutralized with acetic acid. To this residue water (25 mL) was added and extracted 3-fold with 25 mL of $CHCl_3$. The combined organic layers were dried on $Na_2SO_4$, filtered, and concentrated to dryness under reduced pressure. The residue was chromatographed over silica gel ($SiO_2$, 230-400 flash), eluting with a gradient of 20% ethyl acetate in hexane to 40% ethyl acetate in hexane. Concentration provides methyl 8-sec-butyl-6-(3-(4-chlorophenyl)-3-oxoprop-1-enyl)-2-oxo-2H-chromene-3-carboxylate (General Formula IV). (0.49 g, 80% yield). White solid, m. p. 145-146° C.; $^1$H NMR ($CDCl_3$, 300 MHz); δ 8.59 (s, 1H), 7.99 (d, 2H, J=8.5 Hz), 7.84-7.75 (m, 3H), 7.58-7.47 (m, 3H), 4.0 (s, 3H), 3.45-3.36 (m, 1H), 1.78-1.69 (m, 2H), 1.32 (d, 3H, J=7.0 Hz), 0.89 (t, 3H, J=7.3 Hz): $^{13}$C NMR ($CDCl_3$, 75 MHz); δ 188.6, 163.4, 156.1, 154.0, 149.1, 143.1, 139.5, 136.7, 136.2, 131.6, 131.4, 130.0, 129.0, 127.3, 122.3, 118.4, 118.2, 52.9, 33.5, 29.6, 20.4. 12.0; ESI-MS (m/z): 425 (M+H)$^+$.

Example-5

Ethyl 8-sec-butyl-6-(3-(4-chlorophenyl)-3-oxoprop-1-enyl)-2-oxo-2H-chromene-carboxylate (General Formula IV) (See Accompanying Formula Drawing S009-0135)

A solution of 3-sec-butyl-5-(3-(4-chlorophenyl)-3-oxoprop-1-enyl)-2-hydroxybenzaldehyde of formula III (0.5 g, 1.46 mmol), diethyl malonate (0.23 g, 1.46 mmol) in tetrahydrofuran (20 mL) was treated with pyridine (0.4 mL) and refluxed. Most of the excess solvent was evaporated under reduced pressure, and the residue was neutralized with dilute HCl (2 N). To this residue water (30 mL) was added and extracted 3-fold with 25 mL of $CHCl_3$. The combined organic layers were dried on $Na_2SO_4$, filtered, and concentrated to dryness under reduced pressure. The residue was chromatographed over silica gel ($SiO_2$, 230-400 flash), eluting with a gradient of 20% ethyl acetate in hexane to 40% ethyl acetate in hexane, which upon concentration provides ethyl 8-sec-butyl-6-(3-(4-chlorophenyl)-3-oxoprop-1-enyl)-2-oxo-2H-chromene-carboxylate (General Formula IV). (0.51 g, 81% yield). White solid, m. p. 119-120° C.; $^1$H NMR ($CDCl_3$, 300 MHz): δ 8.55 (s, 1H), 7.99 (d, 2H, J=8.6 Hz), 7.84-7.73 (m, 3H), 7.54-7.47 (m, 3H), 4.43 (q, 2H, J=7.1 Hz), 3.45-3.35 (m, 1H), 1.78-1.69 (m, 2H), 1.41 (t, 3H, J=7.1 Hz), 1.32 (d, 3H, J=7.0 Hz), 0.89 (t, 3H, J=7.3 Hz)); $^{13}$C NMR ($CDCl_3$, 75 MHz): δ 188.6, 163.9, 156.2, 154.0, 148.5, 143.2, 139.5, 136.8, 136.3, 131.5, 131.4, 130.0, 129.1, 127.3, 122.3, 118.8, 118.2, 62.1, 33.5, 29.7, 20.4, 14.3, 12.0; ESI-MS (m/z): 439 (M+H)$^+$.

Example-6

Methyl 8-sec-butyl-2-oxo-6-(3-oxo-3-phenylprop-1-enyl)-2H-chromene-3-carboxylate (General Formula IV) (See Accompanying Formula Drawing S009-0133)

A solution of 3-sec-butyl-2-hydroxy-5-(3-oxo-3-phenyl-prop-1-enyl)benzaldehyde of formula III (0.5 g, 1.62 mmol), dimethyl malonate (0.21 g, 1.62 mmol) in methanol (25 mL) was treated with piperidine (0.2 mL) and refluxed. Most of the excess solvent was evaporated under reduced pressure, and the residue was neutralized with acetic acid. To this residue water (25 mL) was added and extracted 3-fold with 20 mL of $CHCl_3$. The combined organic layers were dried on $Na_2SO_4$. filtered, and concentrated to dryness under reduced pressure. The residue was chromatographed over silica gel ($SiO_2$, 230-400 flash), eluting with a gradient of 20% ethyl acetate in hexane to 40% ethyl acetate in hexane, which upon concentration provides methyl 8-sec-butyl-2-oxo-6-(3-oxo-3-phenylprop-1-enyl)-2H-chromene-3-carboxylate (General Formula IV). (0.49 g, 78% yield). White solid, m. p. 139-140° C.; $^1$H NMR ($CDCl_3$, 300 MHz): δ 8.58 (s, 1H), 8.04 (brd, 2H, J=8.5 Hz), 7.83-7.71 (m, 3H), 7.64-7.50 (m, 4H), 3.97 (s, 3H), 3.49-3.37 (m, 1H), 1.78-1.69 (m, 2H), 1.33 (d, 3H, J=7.0 Hz), 0.90 (t, 3H, J=7.4 Hz); $^{13}$C NMR ($CDCl_3$, 75 MHz): δ 190.1, 163.6, 154.0, 149.2, 142.7, 138.0, 136.8, 133.2, 131.7, 131.6, 129.0, 128.8, 128.6, 127.3, 122.0, 118.4, 118.2, 53.0, 33.5, 29.7, 20.5, 12.1; ESI-MS (m/z): 391 (M+H)$^+$.

Example-7

Ethyl 8-sec-butyl-2-oxo-6-(3-oxo-3-phenylprop-1-enyl)-2H-chromene-3-carboxylate (General Formula IV) (See Accompanying Formula Drawing S009-0132)

A solution of 3-sec-butyl-2-hydroxy-5-(3-oxo-3-phenyl-prop-1-enyl)benzaldehyde of formula III (0.5 g, 1.62 mmol), diethyl malonate (0.26 g, 1.62 mmol) in ethanol (20 mL) was treated with N-methyl morpholine (0.2 mL) and refluxed. Most of the excess solvent was evaporated under reduced pressure, and the residue was neutralized with dilute hydrochloric acid (HCl) (2 N). To this residue water (35 mL) was added and extracted 3-fold with 25 mL of $CHCl_3$. The combined organic layers were dried on $Na_2SO_4$, filtered, and concentrated to dryness under reduced pressure. The residue was chromatographed over silica gel ($SiO_2$, 230-400 flash), eluting with a gradient of 20% ethyl acetate in hexane to 40% ethyl acetate in hexane, which upon concentration provides ethyl8-sec-butyl-2-oxo-6-(3-oxo-3-phenylprop-1-enyl)-2H- chromene-3-carboxylate (General Formula IV). (0.52 g, 80% yield). White solid, m. p. 155-156° C.; $^1$H NMR (CDCl$_3$, 300 MHz): δ 8.57 (s, 1H), 8.04 (d, 2H, J=7.1 Hz), 7.84-7.76 (m, 3H), 7.60-7.49 (m, 5H), 4.43 (q, 2H, J=6.2 Hz,), 3.41 (q, 1H, J=6.8 Hz), 1.78-1.68 (m, 2H), 1.41 (t, 3H, J=6.6 Hz), 1.32 (d, 3H, J=6.9 Hz), 0.89 (t, 3H, J=7.2 Hz); $^{13}$C NMR (CDCl$_3$, 75 MHz): δ 189.8, 162.7, 156.1, 153.8, 148.6, 142.6, 137.8, 136.5, 133.0, 131.4, 128.7, 128.5, 127.2, 122.8, 118.6, 118.1, 62.0, 33.4, 29.6, 20.3, 14.2, 11.9; ESI-MS (m/z): 405 (M+H)$^+$. HRMS calcd for C$_{25}$H$_{25}$O$_5$ (M+H)$^+$ 405.1702, Found: 405.1718.

Example-8

Ethyl 8-sec-butyl-2-oxo-6-(3-oxo-3-p-tolylprop-1-enyl)-2H-chromene-3-carboxylate (General Formula IV) (See Accompanying Formula Drawing S009-0131)

A solution of 3-sec-butyl-2-hydroxy-5-(3-oxo-3-p-tolyl-prop-1-enyl)benzaldehyde of formula III (0.5 g, 1.55 mmol), diethylmalonate (0.24 g, 1.55 mmol) in THF (30 mL) was treated with piperidine (0.3 mL) and refluxed. Most of the excess solvent was evaporated under reduced pressure, and the residue was neutralized with acetic acid. To this residue water (40 mL) was added and extracted 3-fold with 30 mL of CHCl$_3$. The combined organic layers were dried on Na$_2$SO$_4$, filtered, and concentrated to dryness under reduced pressure. The residue was chromatographed over silica gel (SiO$_2$, 230-400 flash), eluting with a gradient of 20% ethyl acetate in hexane to 40% ethyl acetate in hexane, which upon concentration provides ethyl 8-sec-butyl-2-oxo-6-(3-oxo-3-p-tolyl-prop-1-enyl)-2H-chromene-3-carboxylate (General Formula IV) (0.51 g, 80% yield). White solid, m. p. 155-156° C.; $^1$H NMR (CDCl$_3$, 300 MHz): δ 8.54 (s, 1H), 7.94 (d, 2H, J=8.1 Hz), 7.81-7.71 (m, 3H), 7.54 (d, 1H, J=15.7 Hz), 7.31 (d, 2H, J=8.0 Hz), 4.43 (q, 2H, J=7.1 Hz), 3.47-3.36 (m, 1H), 2.44 (s, 3H), 1.78-1.69 (m, 2H), 1.42 (t, 3H, J=7.1 Hz), 1.33 (d, 3H, J=7.0 Hz), 0.89 (t, 3H, J=7.4 Hz); $^{13}$C NMR (CDCl$_3$, 75 MHz): δ 189.5, 162.9, 156.3, 153.9, 148.7, 144.1, 142.3, 136.7, 135.4, 131.7, 131.5, 129.5, 128.7, 127.1, 122.9, 118.7, 118.2, 62.1, 33.5, 29.7, 21.5, 20.5, 14.3, 12.1; ESI-MS (m/z): 419 (M+H)$^+$. HRMS calcd for C$_{26}$H$_{27}$O$_5$ (M+H)$^+$ 419.1858, Found: 419.1838.

Example-9

(E)-8-tert-butyl-2-oxo-6-(3-oxo-3-p-tolylprop-1-enyl)-2H-chromene-3-carboxylic Acid (General Formula V)

To a solution of (E)-ethyl 8-tert-butyl-2-oxo-6-(3-oxo-3-p-tolylprop-1-enyl)-2H-chromene-3-carboxylate (0.5 g, 1.19 mmol) in ethanol (50 mL) was added 10% aqueous KOH (10 mL), and the mixture was vigorously stirred for 1 h at room temperature. After completion of the reaction, the solvents were removed and the residue was acidified with dilute hydrochloric acid (HCl) (2 N). The precipitate was separated by filtration and dried over vacuum. The residue was washed with methanol to give (E)-8-tert-butyl-2-oxo-6-(3-oxo-3-p-tolylprop-1-enyl)-2H-chromene-3-carboxylic acid of Formula V (0.31 g, 64% yield).

White solid, m. p. 185-186° C.; $^1$H NMR (DMSO-d6 300 MHz): δ 12.17 (brs, 1H) 7.74 (d, J=8.1 Hz, 2H), 7.61-7.56 (m, 3H), 7.44 (d, J=1.7 Hz, 1H), 7.32 (d, J=15.7 Hz, 1H), 7.12 (d, J=8.0 Hz, 2H), 2.25 (s, 3H), 1.35 (brs, 9H); $^{13}$C NMR (DMSO-d6, 75 MHz): δ 189.4, 166.2, 157.4, 154.1, 143.7, 142.4, 141.9, 138.9, 135.3, 131.2, 129.8, 129.4, 128.7, 126.4, 126.2, 122.6, 119.3, 35.1, 30.1, 21.3; ESI-MS (m/z): 389 (M–H)$^-$.

Example-10

(E)-8-tert-butyl-N,N-diethyl-2-oxo-6-(3-oxo-3-p-tolylprop-1-enyl)-2H-chromene-3-carboxamide (General Formula VI) (See Accompanying Formula Drawing S010-1992)

To a suspension of (E)-8-tert-butyl-2-oxo-6-(3-oxo-3-p-tolylprop-1-enyl)-2H-chromene-3-carboxylic acid of the formula (V) (0.5 g, 1.28 mmol) in benzene (10 mL), added thionyl chloride (1.0 mL), was refluxed for 2 h. The resulting solution was evaporated to dryness under reduced pressure, and the residue was dispersed in benzene (10 mL). The solvent was eliminated under reduced pressure. Dispersion in solvent and solvent elimination was repeated twice. The residue was dissolved in organic solvent benzene (10 mL) and added with stirring to a solution of the diethyl amine (0.09 g, 1.28 mmol). After 30 min at room temperature, the solvent was removed by evaporation under reduced pressure and extracted 3-fold with CHCl$_3$ (30 mL). The combined organic layers were dried on Na$_2$SO$_4$, filtered, and concentrated to dryness under reduced pressure. The residue was chromatographed over silica gel (SiO$_2$, 230-400 flash), eluting with a gradient of 20% ethyl acetate in hexane to 40% ethyl acetate in hexane, which upon concentration provides (E)-8-tert-butyl-N,N-diethyl-2-oxo-6-(3-oxo-3-p-tolylprop-1-enyl)-2H-chromene-3-carboxamide (General Formula VI). (0.37 g, 65% yield). White solid, m. p. 170-171° C.; $^1$H NMR (CDCl$_3$ 300 MHz): δ 7.94 (d, J=8.1 Hz, 2H), 7.81-7.76 (m, 3H), 7.64 (d, J=1.7 Hz, 1H), 7.52 (d, J=15.7 Hz, 1H), 7.32 (d, J=8.0 Hz, 2H), 3.57 (q, J=7.1 Hz, 2H), 3.34 (q, J=7.0 Hz, 2H), 2.45 (s, 3H), 1.55 (brs, 9H), 1.28 (t, J=7.1 Hz, 3H), 1.21 (t, J=7.1 Hz, 3H); $^{13}$C NMR (CDCl$_3$, 75 MHz): δ 189.7, 164.3, 157.3, 153.8, 144.0, 142.8, 141.7, 138.9, 135.4, 131.3, 129.8, 129.5, 128.8, 126.6, 126.2, 122.8, 119.2, 43.4, 39.6, 35.2, 29.8, 21.8, 14.3, 12.8; ESI-MS (m/z): 446 (M+H)$^+$.

Example-11

(E)-8-sec-butyl-N-methyl-2-oxo-6-(3-oxo-3-p-tolyl-prop-1-enyl)-2H-chromene-3-carboxamide (General Formula VI) (See Accompanying Formula Drawing S010-1994)

To a suspension of (E)-8-sec-butyl-2-oxo-6-(3-oxo-3-p-tolylprop-1-enyl)-2H-chromene-3-carboxylic acid of the formula (V) (0.5 g, 1.28 mmol) in CCl$_4$ (15 mL), added thionyl chloride (1.0 mL), was refluxed for 2.5 h. The resulting solution was evaporated to dryness under reduced pressure, and the residue was dispersed in CCl$_4$ (10 mL). The solvent was eliminated under reduced pressure. Dispersion in CCl$_4$ and solvent elimination was repeated twice. The residue was dissolved in CCl$_4$ (10 mL) and added with stirring to a solution of the methyl amine (0.04 g, 1.28 mmol). After 40 min at room temperature, the solvent was removed by evaporation under reduced pressure and extracted 3-fold with CHCl$_3$ (25 mL). The combined organic layers were dried on Na$_2$SO$_4$, filtered, and concentrated to dryness under reduced pressure. The residue was chromatographed over silica gel (SiO$_2$, 230-400 flash), eluting with a gradient of 20% ethyl acetate in hexane to 40% ethyl acetate in hexane, which upon concentration provides (E)-8-sec-butyl-N-methyl-2-oxo-6-(3-oxo-3-p-tolylprop-1-enyl)-2H-chromene-3-carboxamide (General Formula VI). (0.33 g, 65% yield). White solid, m. p. 215-216° C.; $^1$H NMR (CDCl$_3$ 300 MHz): δ 8.93 (s, 1H), 8.72, (brd, J=4.6 Hz, 1H) 7.96 (d, J=8.1 Hz, 2H), 7.83-7.77 (m, 3H), 7.55 (d, J=15.7 Hz, 1H), 7.33 (d, J=8.0 Hz, 2H), 3.49-3.37 (m, 1H), 3.04 (d, J=4.9 Hz, 3H), 2.45 (s, 3H), 1.80-1.71 (m, 2H), 1.35 (d, J=6.9 Hz, 3H), 0.94 (t, J=7.4 Hz, 3H); $^{13}$C NMR (CDCl$_3$, 75 MHz): δ 189.5, 1610, 161.2, 153.1, 148.5, 144.1, 142.2, 136.5, 135.4, 132.2, 131.4, 129.5, 128.8, 127.1, 123.2, 119.0, 118.8, 33.6, 29.8, 26.7, 21.8, 20.6, 12.1; ESI-MS (m/z): 404 (M+H)$^+$.

Example-12

(E)-8-sec-butyl-N-ethyl-2-oxo-6-(3-oxo-3-p-tolyl-prop-1-enyl)-2H-chromene-3-carboxamide (General Formula VI) (See Accompanying Formula Drawing S010-1995)

To a suspension of (E)-8-sec-butyl-2-oxo-6-(3-oxo-3-p-tolylprop-1-enyl)-2H-chromene-3-carboxylic acid of the formula (V) (0.5 g, 1.28 mmol) in toluene (15 mL), added thionyl chloride (1.0 mL), was refluxed for 3 h. The resulting solution was evaporated to dryness under reduced pressure, and the residue was dispersed in toluene (15 mL). The solvent was eliminated under reduced pressure. Dispersion in toluene and solvent elimination was repeated twice. The residue was dissolved toluene (10 mL) and added with stirring to a solution of the ethyl amine (0.06 g, 1.28 mmol). After 35 min at room temperature, the solvent was removed by evaporation under reduced pressure and extracted 3-fold with CHCl$_3$ (20 mL). The combined organic layers were dried on Na$_2$SO$_4$, filtered, and concentrated to dryness under reduced pressure. The residue was chromatographed over silica gel (SiO$_2$, 230-400 flash), eluting with a gradient of 20% ethyl acetate in hexane to 40% ethyl acetate in hexane, which upon concentration provides (E)-8-sec-butyl-N-ethyl-2-oxo-6-(3-oxo-3-p-tolylprop-1-enyl)-2H-chromene-3-carboxamide (General Formula VI). (0.34 g, 64% yield). White solid, m. p. 162-163° C.; $^1$H NMR (CDCl$_3$ 300 MHz): δ 8.93 (s, 1H), 7.96 (d, J=8.2 Hz, 2H), 7.83-7.76 (m, 3H), 7.54 (d, J=15.7 Hz, 2H), 7.33 (d, J=8.0 Hz, 2H), 3.57-3.39 (m, 3H), 2.45 (s, 3H), 1.80-1.73 (m, 2H), 1.34 (d, J=6.9 Hz, 3H), 1.28 (t, J=7.3 Hz, 3H). 0.91 (t, J=7.3 Hz, 3H); $^{13}$C NMR (CDCl$_3$, 75 MHz): δ 189.6, 161.2, 161.1, 153.1, 148.5, 144.1, 142.3, 136.5, 135.4, 132.2, 131.4, 128.8, 127.1, 123.2, 119.1, 119.0, 122.8, 34.9, 33.7, 29.8, 21.8, 20.6, 14.8, 12.1; ESI-MS (m/z): 418(M+H)$^+$.

Example-13

(E)-8-sec-butyl-N,N-diethyl-2-oxo-6-(3-oxo-3-p-tolylprop-1-enyl)-2H-chromene-3-carboxamide (General Formula VI) (See Accompanying Formula Drawing S010-1996)

To a suspension of (E)-8-sec-butyl-2-oxo-6-(3-oxo-3-p-tolylprop-1-enyl)-2H-chromene-3-carboxylic acid of the formula (V) (0.5 g, 1.28 mmol) in dichloromethane (20 mL). added thionyl chloride (1.0 mL), was refluxed for 1.5 h. The resulting solution was evaporated to dryness under reduced pressure, and the residue was dispersed in dichloromethane (10 mL). The solvent was eliminated under reduced pressure. Dispersion in dichloromethane and solvent elimination was repeated twice. The residue was dissolved in dichloromethane (15 mL) and added with stirring to a solution of the diethyl amine (0.09 g, 1.28 mmol). After 45 min at room temperature, the solvent was removed by evaporation under reduced pressure and extracted 3-fold with CHCl$_3$ (25 mL). The combined organic layers were dried on Na$_2$SO$_4$, filtered, and concentrated to dryness under reduced pressure. The residue was chromatographed over silica gel (SiO$_2$, 230-400 flash), eluting with a gradient of 20% ethyl acetate in hexane to 40% ethyl acetate in hexane, which upon concentration provides (E)-8-sec-butyl-N,N-diethyl-2-oxo-6-(3-oxo-3-p-tolylprop-1-enyl)-2H-chromene-3-carboxamide (General Formula VI). (0.37 g, 65% yield). White solid, m. p. 146-147° C.; $^1$H NMR (CDCl$_3$ 300 MHz): δ 7.95, (d, J=8.1 Hz, 2H) 7.82-7.76 (m, 2H), 7.70 (d, J=1.8 Hz, 1H), 7.59 (d, J=1.8 Hz, 1H), 7.51 (d, J=15.7 Hz, 1H), 7.33 (d, J=8.0 Hz, 2H), 3.58 (q, J=7.0 Hz, 2H), 3.45-3.41 (m, 1H), 3.33 (q, J=7.1 Hz, 2H), 2.45 (brs, 3H), 1.79-1.72 (m, 2H) 1.34-1.25 (m, 6H), 1.20 (t, J=7.1 Hz, 3H) 0.89 (t, J=7.4 Hz, 3H); $^{13}$C NMR (CDCl$_3$, 75 MHz): δ 189.7, 164.3, 157.8, 152.7, 144.0, 142.6, 141.4, 136.7, 135.5, 131.7, 129.8, 129.5, 128.8, 126.7, 126.0, 122.9, 118.7, 43.4, 39.6, 33.5, 29.8, 21.8, 20.6, 14.3, 12.9, 12.1; ESI-MS (m/z): 446 (M+H)$^+$.

Example-14

(E)-ethyl 8-sec-butyl-2-oxo-6-(3-oxo-3-(3,4,5-trimethoxyphenyl)prop-1-enyl)-2H-chromene-3-carboxylate (General Formula IV) (See Accompanying Formula Drawing S010-2000)

A solution of (E)-3-sec-butyl-2-hydroxy-5-(3-oxo-3-(3,4,5-trimethoxyphenyl)prop-1-enyl)benzaldehyde of formula III (0.5 g, 1.26 mmol), diethyl malonate (0.20 g, 1.26 mmol) in ethanol (30 mL) was treated with piperidine (0.2 mL) and refluxed. Most of the excess solvent was evaporated under reduced pressure, and the residue was neutralized with acetic acid. To this residue water (35 mL) was added and extracted 3-fold with 15 mL of CHCl$_3$. The combined organic layers were dried on Na$_2$SO$_4$, filtered, and concentrated to dryness under reduced pressure. The residue was chromatographed over silica gel (SiO$_2$, 230-400 flash), eluting with a gradient of 20% ethyl acetate in hexane to 40% ethyl acetate in hexane, which upon concentration provides (E)-ethyl 8-sec-butyl-2-oxo-6-(3-oxo-3-(3,4,5-trimethoxyphenyl)prop-1-enyl)-2 H-chromene-3-carboxylate (General Formula IV). (0.49 g, 78% yield). White solid, m. p. 128-129° C.; $^1$H NMR (CDCl$_3$ 300 MHz): δ 8.56 (s, 1H), 7.83-7.75 (m, 3H), 7.49 (d, J=15.6 Hz, 1H), 7.31-7.29 (m, 2H), 4.42 (q, J=7.1 Hz, 2H), 3.95 (brs, 9H), 3.45-3.36 (m, 1H), 1.78-1.69 (m, 2H), 1.42 (t, J=7.1 Hz, 3H) 3.33 (d, J=6.9 Hz, 3H) 0.89 (t, J=7.3 Hz, 3H); $^{13}$C NMR (CDCl$_3$, 75 MHz): δ 188.8, 162.9, 156.3, 153.9, 153.3, 148.6, 142.9, 142.7, 136.7, 133.2, 131.8, 131.6, 126.8, 122.7, 118.8, 118.2, 106.4, 62.1, 61.1, 56.6, 50.8, 33.6, 29.7, 20.5, 14.3, 12.1; ESI-MS (m/z): 495 (M+H)$^+$.

Example-15

(E)-methyl 8-sec-butyl-2-oxo-6-(3-oxo-3-(3,4,5-trimethoxyphenyl)prop-1-enyl)-2H-chromene-3-carboxylate (General Formula IV) (See Accompanying Formula Drawing S010-2001)

A solution of (E)-3-sec-butyl-2-hydroxy-5-(3-oxo-3-(3,4,5-trimethoxyphenyl)prop-1-enyl)benzaldehyde of formula III (0.5 g, 1.26 mmol), dimethyl malonate (0.20 g, 1.26 mmol) in methanol (20 mL) was treated with N-methyl morpholine (0.3 mL) and refluxed. Most of the excess solvent was evaporated under reduced pressure, and the residue was neutralized with acetic acid. To this residue water (30 mL) was added and extracted 3-fold with 25 mL of CHCl$_3$. The combined organic layers were dried on Na$_2$SO$_4$, filtered, and concentrated to dryness under reduced pressure. The residue was chromatographed over silica gel (SiO$_2$, 230-400 flash), eluting with a gradient of 20% ethyl acetate in hexane to 40% ethyl acetate in hexane hexane, which upon concentration provides (E)-methyl 8-sec-butyl-2-oxo-6-(3-oxo-3-(3,4,5-trimethoxyphenyl)prop-1-enyl)-2H-chromene-3-carboxylate (General Formula IV) (0.48 g, 79% yield). White solid, m. p. 138-139° C.; $^1$H NMR (CDCl$_3$ 300 MHz): δ 8.59 (s, 1H), 7.84-7.73 (m, 3H), 7.48 (d, J=15.6 Hz, 1H), 7.29 (brs, 2H), 3.95 (brs, 12H), 3.48-337 (m, 1H), 1.78-1.69 (m, 2H), 3.33 (d, J=6.9 Hz, 3H) 0.89 (t, J=7.3 Hz, 3H); $^{13}$C NMR (CDCl$_3$, 75 MHz): δ 188.8, 163.6, 156.2, 154.0, 153.3, 149.2, 143.0, 142.6, 136.7, 133.2, 131.9, 131.7, 126.9, 122.8, 118.4, 118.2, 106.5, 61.2, 56.6, 53.0, 33.6, 29.7, 20.5, 12.1; ESI-MS (m/z): 481 (M+H)$^+$.

Example-16

(E)-methyl 8-tert-butyl-2-oxo-6-(3-oxo-3-(3,4,5-trimethoxyphenyl)prop-1-enyl)-2H-chromene-3-carboxylate (General Formula IV) (See Accompanying Formula Drawing S010-2003)

A solution of (E)-3-tert-butyl-2-hydroxy-5-(3-oxo-3-(3,4,5-trimethoxyphenyl)prop-1-enyl)benzaldehyde of formula III (0.5 g, 1.26 mmol), dimethyl malonate (0.20 g, 1.26 mmol) in THF (20 mL) was treated with pyridine (0.4 mL) and refluxed. Most of the excess solvent was evaporated under reduced pressure, and the residue was neutralized with acetic acid. To this residue water (40 mL) was added and extracted 3-fold with 20 mL of CHCl$_3$. The combined organic layers were dried on Na$_2$SO$_4$, filtered, and concentrated to dryness under reduced pressure. The residue was chromatographed over silica gel (SiO$_2$, 230-400 flash), eluting with a gradient of 20% ethyl acetate in hexane to 40% ethyl acetate in hexane, which upon concentration provides (E)-methyl 8-tert-butyl-2-oxo-6-(3-oxo-3-(3,4,5-trimethoxyphenyl)prop-1-enyl)-2H-chromene-3-carboxylate (General Formula IV). (0.48 g, 79% yield). White solid, m. p. 145-146° C.; $^1$H NMR (CDCl$_3$ 300 MHz): δ 8.57 (s, 1H), 7.86 (d, J=1.7 Hz, 1H), 7.84-7.78 (m, 1H) 7.74 (d, J=1.6 Hz, 1H), 7.47 (d, J=15.6 Hz, 1H), 7.28 (s, 2H), 3.96 (brs, 12H), 1.55 (s, 9H); $^{13}$C NMR (CDCl$_3$, 75 MHz): δ 188.8, 163.6, 155.7, 155.1, 153.3, 149.5, 143.0, 142.8, 139.1, 133.3, 131.8, 131.3, 127.4, 122.7, 118.8, 118.0, 106.4, 61.1, 56.6, 53.0, 35.0, 29.7; ESI-MS (m/z): 481 (M+H)$^+$.

BIOLOGICAL EVALUATION

To study the in vitro anticancer activity of coumarin/chalcones, we first screened the individual chalcone (S008-392), coumarin (S009-0139), and their combination (S008-0392+ S009-0139 (1:1 molar ratio)), along with a coumarin/chalcone hybrid (S009-0131) against the human cervical cancer cell line—C33A and the non-cancer (mouse embryo fibroblast) cells—NIH3T3. The results shown in Table 1 clearly indicate that coumarin/chalcone hybrid (S009-0131) is not only active against the C33A cell line (IC50=3.59 μM) but is also non toxic to the fibroblast cells NIH3T3 (IC$_{50}$>150 uM). We thus synthesized a variety of coumarin/chalcone derivatives which were evaluated for their in vitro anticancer activity against four human cancer cell lines, KB (oral squamous cell carcinoma), C33A (cervical carcinoma), MCF-7 (breast adenocarcinoma). A549 (lung) and the non-cancer (fibroblast) cells NIH3T3 in order to determine their cyto-selective nature. The results presented in Table 2 show that among all active compounds, S009-0131 was most selective (poor activity or lack of activity against other cell lines) as well as highly active against cervical cancer (C33A). The compounds having IC$_{50}$ value more than 150 μM, were considered inactive. In this assay. Doxorubicin and Tamoxifen were used as reference drugs.

TABLE 1

IC$_{50}$ (μM) values of representative examples of the invention

| Example | C33A (cervical cancer) | NIH3T3 (mouse fibroblast) |
|---|---|---|
| S008-0392 (chalcone) | 10.24 | 128.65 |
| S009-0139 (coumarin) | 64.30 | NA |
| S008-0392 + S009-0139 (1:1 molar ratio) | 13.83 | NA |
| S009-0131 (coumarin/chalcone) | 3.59 | NA |

NA = Not active (IC$_{50}$ > 150 μM)

TABLE 2

IC$_{50}$ (μM) values of representative examples of the invention and reference compounds

| Example or Reference | KB (Oral) | C33A (Cervical) | MCF-7 (Breast) | A549 (Lung) | NIH3T3 (Non-cancer, fibroblast) |
|---|---|---|---|---|---|
| S009-0139 | 131.59 | 64.30 | 112.89 | 146.82 | NA |
| S009-0136 | 28.25 | 5.90 | 10.80 | 16.67 | 42.41 |
| S009-0135 | 14.29 | 4.54 | 11.07 | 12.85 | 38.42 |
| S009-0133 | 13.41 | 6.28 | 11.41 | 10.69 | NA |
| S009-0132 | 10.47 | 8.12 | 88.09 | 12.87 | NA |
| S009-0131 | 17.97 | 3.59 | 81.10 | 32.80 | NA |
| S010-1992 | 2.02 | 1.53 | <7.01 | 1.50 | NA |
| S010-1995 | 10.71 | 5.56 | 22.20 | NA | NA |
| S010-1996 | 3.55 | 3.12 | <7.01 | 3.77 | NA |
| S010-2000 | 9.36 | 5.72 | 11.45 | 11.57 | NA |
| S010-2001 | 3.10 | 2.56 | 10.16 | 3.68 | NA |
| S010-2003 | 8.30 | 4.99 | 13.26 | 11.07 | NA |
| Doxorubicin | 0.22 | 0.82 | 0.61 | 0.52 | ND |
| Tamoxifen | ND | ND | 11.8 | ND | ND |

ND = Not done, NA = Not active (IC$_{50}$ > 150 μM)

In vivo Antitumor Activity of Compounds

Experiments with human tumor xenografts in SCID mice were done to evaluate the ability of compounds of this invention to inhibit tumor growth in vivo. In mice bearing human cervical cancer cells (HeLa), the Relative Tumor Volume (Table 3) and Tumor Growth Inhibition Index (Table 4) values show that oral administration of S009-0131 caused a significant reduction of tumor volumes relative to the vehicle control. In this respect, the activity of S009-0131 was somewhat better than that of the standard drug adriamycin. S009-0131 was apparently non-toxic to the animals as they did show any loss of weight during the period of the study (Table-5).

TABLE 3

In vivo activity of example S009-0131 in the human tumor xenograft with mice bearing HeLa Human cervical cancer cells (RTV values)

| Days | Control | ADR 2 mg/kg I.V. Q7dx3 | S009-0131, 100 mg/kg, p.o. daily up to 15 days |
|---|---|---|---|
| 1 | 1 | 1 | 1 |
| 5 | 1.31 | 0.69 | 0.76 |
| 9 | 1.65 | 0.72 | 0.79 |
| 12 | 1.96 | 0.92 | 1.21 |
| 15 | 3.26 | 1.39 | 1.28 |
| 19 | 3.64 | 1.65 | 1.01 |
| 22 | 5.21 | 3.52 | 1.73 |
| 25 | 6.24 | 3.84 | 1.82 |

TABLE 3-continued

In vivo activity of example S009-0131 in the human tumor xenograft
with mice bearing HeLa Human cervical cancer cells (RTV values)

| Days | Control | ADR 2 mg/kg I.V. Q7dx3 | S009-0131, 100 mg/kg, p.o. daily up to 15 days |
|---|---|---|---|
| 29 | 7.34 | 4.60 | 2.39 |
| 33 | 10.00 | 4.69 | 4.20 |

ADR = Adriamycin (Doxorubicin) standard drug used

TABLE 4

In vivo activity of example S009-0131 in the human tumor xenograft with
SCID mice bearing HeLa Human cervical cancer cells (T/C Values)

| Days | ADR 2 mg/kg I.V. Q7dx3 | S009-0131, 100 mg/kg, daily oral upto 15 days |
|---|---|---|
| 1 | 1 | 1 |
| 5 | 0.53 | 0.58 |
| 9 | 0.44 | 0.48 |
| 12 | 0.47 | 0.61 |
| 15 | 0.43 | 0.39 |
| 19 | 0.45 | 0.28 |
| 22 | 0.68 | 0.33 |
| 25 | 0.62 | 0.29 |
| 29 | 0.63 | 0.33 |
| 33 | 0.47 | 0.42 |
| 37 | 0.58 | 0.42 |
| 41 | 0.49 | 0.44 |
| 44 | 0.43 | 0.45 |
| 51 | 0.43 | 0.38 |

ADR = Adriamycin (Doxorubicin) standard drug used

TABLE 5

Average Animal weight (grams)

| Days | Control | ADR 2 mg/kg I.V. Q7dx3 | S009-0131, 100 mg/kg, daily oral up to 15 days |
|---|---|---|---|
| 1 | 21.2 | 20.7 | 24.2 |
| 5 | 21.4 | 20.9 | 24.2 |
| 9 | 21.9 | 20.6 | 23.5 |
| 12 | 22.0 | 20.3 | 18.5 |
| 15 | 21.7 | 19.6 | 22.6 |
| 19 | 21.9 | 18.3 | 22.4 |
| 22 | 22.3 | 19.7 | 23.0 |
| 25 | 22.5 | 19.9 | 23.2 |
| 29 | 22.6 | 20.4 | 23.6 |
| 33 | 22.3 | 20.6 | 23.3 |
| 37 | 22.8 | 24.8 | 23.0 |
| 41 | 23.1 | 21.8 | 23.4 |
| 44 | 23.5 | 22.1 | 23.8 |
| 51 | 23.4 | 21.2 | 23.4 |

ADR = Adriamycin (Doxorubicin) standard drug used

EXPERIMENTATION

1. Determination of in vitro Anti-Cancer Efficacy Using Human Cancer Cell Lines

The human cancer cell lines—KB (oral squamous cell carcinoma). C33A (cervical carcinoma), MCF-7 (breast adenocarcinoma), A549 (lung carcinoma) and mouse embryo fibroblast (NIH3T3) were obtained from American Type Culture Collection (ATCC), USA. These cells were grown in recommended media supplemented with 10% FBS, 50 µg/mL gentamycin and 2.5 µg/mL amphotericin B in a 5% $CO_2$ humidified atmosphere at 37° C. Cells below 15 passage level were used for this study. A colorimetric sulforhodamine B assay was used for the measurement of cell cytotoxicity. $1\times10^4$ cells (in 180 µL) were added to each well of 96-well plate and incubated overnight to allow for cell attachment. Cells were then treated with serial two-fold dilutions of test compounds (100 to 1.6 µM) and untreated cells receiving the same volume of medium served as control. After 48 h of exposure, cells were fixed with ice-cold 50% TCA, stained with 0.4% (w/v) SRB in 1% acetic acid, washed and air dried. Bound dye was dissolved in 150 µL of 10 mM tris base. The plates were read at 540 nm absorbance on plate reader (Polarstar Galaxy, BMG, Germany). The cytotoxic effects of compounds were calculated as % inhibition in cell growth as per the formula [100−(Absorbance of compound treated cells/Absorbance of untreated cells)]×100. Determination of 50% inhibitory concentration ($IC_{50}$) was based on dose-response curves.

2. Determination of in vivo Anti-Cancer Efficacy in Human Xenograft Model in SCID Mice The in vivo efficacy studies were performed using human tumor xenografts in SCID mice. Human cervical cancer cells (HeLa) were injected subcutaneously ($1\times10^7$ cells in 100 µl HBSS medium) on the right flank of each mouse. Tumor bearing mice were divided randomly into treatment groups and the treatment schedules began on day 7 of the xenograft. The test compound (S009-0131) was administered orally to each mouse at a daily dose of 100 mg/kg body weight, for 15 days. The standard anti-cancer drug Adriamycin (ADR) was used as 'positive' control and given to each mouse as an i.v. dose of 2 mg/kg body weight, Q7dx3 (3 doses per week, till the end of the study). The group of vehicle treated animals served as 'negative' control.

The tumor volume, body weight and signs of overt toxicity were monitored and recorded for the entire duration of the experiment (60 days). Tumor volumes were calculated using the formula $(a\times b^2)/2$, where a, b are two longest perpendicular diameters. Tumor growth was expressed in terms of relative tumor volume (RTV) which is the ratio of tumor volume on a particular day to the tumor volume on day 1 of the study. Tumor growth inhibition index (T/C) was calculated as follows:

$$T/C = \text{Average } RTV \text{ of test group mice/Average } RTV \text{ of control group mice.}$$

Advantage of the Invention

1. These compounds can be employed for various cancer cell lines without affecting normal cell lines. Due to their cytoselective nature, the compounds are potent and safe anticancer agents.
2. The process described in this invention does not use any extreme conditions of temperature and pressure and thus the process is adaptable to commercial production of the said coumarin-chalcones with anticancer activity.
3. No toxic chemicals and solvents have been used in the process of synthesizing of coumarin-chalcones and thus the process is eco-friendly.

We claim:

1. A compound of general formula (VI) or a pharmaceutically acceptable salt thereof,

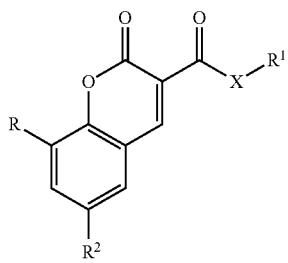

wherein:
R is selected from the group consisting of:
H, CHO, COCH₃, NHCOCH3, F, Cl, Br, NO₂, CF₃, OCF₃, CH₃, C₂H₅, C₃H₇, straight or branched alkyl chain up to six carbons, straight and branched alkoxy/sulphoxy chain up to six carbons, and phenyl and substituted phenyl ring, wherein the substituents in phenyl ring are selected from the group consisting of F, Cl, Br, NO₂, CF₃, CH₃, C₂H₅, C₃H₇, straight or branched alkyl chain up to six carbons,
X is selected from the group consisting of:
O, S, CH₂, and NR³, wherein R³═H, CH₃, C₂H₅, or C₃H₇,
R¹ is selected from the group consisting of:
CH₃, C₂H₅, C₃H₇, straight and branched alkyl chain up to eight carbons, cyclopentyl, cyclohexyl, pipendinyl, unsubstituted and substituted phenyl ring, wherein the substituents in phenyl ring are selected from the group consisting of F, Cl, Br, NO₂, CF₃, CH₃, OCH₃, OC₂H₅, and OCF₃,
R² is selected from the group consisting of:
CHO, and —CH═CHCOR⁴
wherein R⁴ is selected from the group consisting of:
CH₃, C₂H₅, C₃H₇, straight and branched alkyl chain up to eight carbons, cyclopentyl, cyclohexyl, heteroaryl, pipendinyl, thienyl, furyl, pyridyl, indolyl and phenyl, which may be unsubtituted or substituted by one, two or three substituents being independently selected from the group consisting of F, Cl, Br, NO₂, CF₃, CH₃, C₂H₅, OCH₃, OC₂H₅, CF3, NMe₂, NEt₂, SCH₃, and NHCOCH₃.

2. The compound as claimed in claim 1, useful as an anticancer agent for the treatment or prevention of cervical carcinoma, oral squamous cell carcinoma or lung or prostate carcinoma or brain tumor.

3. The compound as claimed in claim 1, wherein the compound is selected from the group consisting of:
I. Ethyl 8-sec-butyl-2-oxo-6-(3-oxo-3-p-tolylprop-1-enyl)-2H-chromene-3-carboxylate (S-009-0131),
II. Ethyl 8-sec-butyl-2-oxo-6-(3-oxo-3-phenylprop-1-enyl)-2H-chromene-3-carboxylate (S-009-0132),
III. Methyl 8-sec-butyl-2-oxo-6-(3-oxo-3-phenylprop-1-enyl)-2H-chrofnene-3-carboxylate (S-009-0133),
IV. Ethyl 8-sec-butyl-6-(3-(4-chlorophenyl)-3-oxoprop-1-enyl)-2-oxo-2H-chromene-3-carboxylate (S-009-0135),
V. Methyl 8-sec-butyl-6-(3-(4-chlorophenyl)-3-oxoprop-1-enyl)-2-oxo-2H-chromene-3-carboxylate (S-009-0136),
VI. (E)-8-tert-Butyl-N.N-diethyl-2-oxo-6-(3-oxo-3-p-tolylprop-1-enyl)-2H-chromene-3-carboxamide (S-010-1992),
VII. (E)-8-sec-Butyl-N-methyl-2-oxo-6-(3-oxo-3-p-tolylprop-1-enyl)-2H-chromene-3-carboxamide (S-010-1994),
VIII. (E)-8-sec-Butyl-N-ethyl-2-oxo-6-(3-oxo-3-p-tolylprop-1-enyl)-2H-chromene-3-carboxamide (S-010-1995),
IX. (E)-8-sec-Butyl-N.N-diethyl-2-oxo-6-(3-oxo-3-p-tolylprop-1-enyl)-2H-chromene-3-carboxamide (S-010-1996),
X. (E)-Ethyl sec-butyl-2-oxo-6-(3-oxo-3-(3,4,5-trimethoxyphenyl)prop-1-enyl)-2H-chromene-3-carboxylate (S-010-2000),
XI. (E)-Methyl sec-butyl-2-oxo-6-(3-oxo-3-(3,4,5-trimethoxyphenyl)prop-1-enyl)-2H-chromene-3-carboxylate (S-010-2001),
XII. (E)-Methyl sec-butyl-2-oxo-6-(3-oxo-3-(3,4,5-trimethoxyphenyl)prop-1-enyl)-2H-chromene-3-carboxylate (S-010-2003), and
XIII. Ethyl 8-sec-butyl-6-formyl-2-oxo-2-H-chromene-3-carboxylate.

4. The compound as claimed in claim 1, wherein R²═CHO; or X═NR³ and R²═CH═CHCOR⁴.

5. A pharmaceutical composition comprising the compound of general formula (VI) as defined in claim 1 or a pharmaceutically acceptable salt thereof.

6. The pharmaceutical composition of claim 1, further comprising an excipient, a diluent, a binder, a solvate, or combinations thereof.

7. A process for preparing a compound of general formula II comprising the steps of:
(i) reacting a compound of the formula (I) wherein R is selected from the group consisting of H, CHO, COCH3, NHCOCH3, F, Cl, Br, NO₂, CF₃, OCF₃, CH₃, C₂H₅, C3H7, straight and branched alkyl chain up to six carbons, straight and branched alkoxy/sulphoxy chain up to six carbons, phenyl and substituted phenyl ring, wherein the substituents in phenyl ring are selected from the group consisting of F, Cl, Br, NO₂, CF₃,CH3, C₂H₅, C₃H₇, straight and branched alkyl chain up to six carbons, with an active methylene compound (in 1:1 to 1:1.2 ratio) selected from diethylmalonate and dimethylmalonate, in an organic solvent in presence of a base at a temperature in the range between 40° C. to 120° C. for a period ranging between 1 to 8 hrs;
(ii) removing the excess solvent under reduced pressure to obtain a residue, (iii) neutralizing the residue with an acid to a pH 6.5-8.0;
(iv) adding water and extracting the mixture with a water immiscible solvent selected from the group consisting of chloroform, dichloromethane, ethyl acetate, and diethyl ether;
(v) removing the solvent to dryness under reduced pressure and purifying the product by chromatographic methods to furnish compound of the formula (II), wherein R is selected from the group consisting of H, CHO, COCH3, NHCOCH3, F, Cl, Br, NO₂, CF₃, OCF₃, CH₃, C₂H₅, C3H7, straight and branched alkyl chain up to six carbons, straight and branched alkoxy/sulphoxy chain up to six carbons, phenyl and substituted phenyl ring, wherein the substituents in phenyl ring are selected from the group consisting of F, Cl, Br, NO₂, CF₃, CH₃, C₂H₅, C₃H₇, straight and branched alkyl chain up to six carbons, and R¹ may be selected from the group of consisting of CH₃, C₂H₅, C₃H₇, straight and branched alkyl chain up to eight carbons, cyclopentyl, cyclohexyl, pipeNdinyl, unsubstituted and substituted phenyl ring, wherein the substituents in phenyl ring are selected from the group consisting of F, Cl, Br, NO₂, CF₃, CH₃, C₂H₅, OCH₃, OC₂H₅, and OCF₃

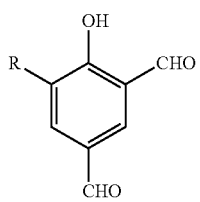

Formula I

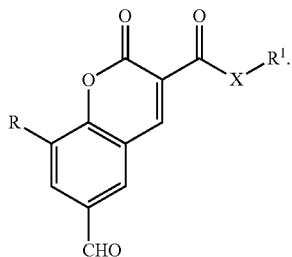

Formula II

8. A process for preparing a compound of general formula VII

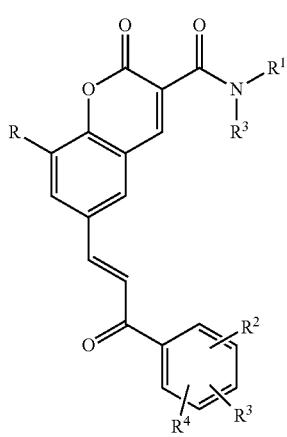

Formula VII wherein
R is selected from the group consisting of H, CHO, COCH$_3$, NHCOCH$_3$, F, Cl, Br, NO$_2$, CF$_3$, OCF$_3$, CH$_3$, C$_2$H$_5$, C$_3$H$_7$, straight and branched alkyl chain up to six carbons, straight and branched alkoxy/sulphoxy chain up to six carbons, phenyl and substituted phenyl ring, wherein the substituents in phenyl ring are selected from the group consisting of F, Cl, Br, NO$_2$, CF$_3$, CH$_3$, C$_2$H$_5$, C$_3$H$_7$, straight and branched alkyl chain up to six carbons, R$^1$ is selected from the group consisting of CH$_3$, C$_2$H$_5$, C$_3$H$_7$, straight and branched alkyl chain up to eight carbons, cyclopentyl, cyclohexyl, pipendinyl, unsubstituted and substituted phenyl ring, wherein the substituents in phenyl ring are selected from the group consisting of F, Cl, Br, NO$_2$, CF$_3$, CH$_3$, C$_2$H$_5$, OCH$_3$, OC$_2$H$_5$, and OCF$_3$, R$^2$, R$^3$, R$^4$ which may be unsubtituted or substituted by one, two or three substituents being independently selected from the group of consisting of F, Cl, Br, NO$_2$, CF$_3$, CH$_3$, C$_2$H$_5$, OCH$_3$, OC$_2$H$_5$, CF$_3$, NMe$_2$, NEt$_2$, SCH$_3$, and NHCOCH$_3$, with the proviso when R$^3$ is attached to N, then R$^3$=H, CH$_3$, C$_2$H$_5$ or C$_3$H$_7$, the process comprising the steps of:

(i) reacting a compound of formula (I) wherein R is selected from the group consisting of H, CHO, COCH$_3$, NHCOCH$_3$, F, Cl, Br, NO$_2$, CF$_3$, OCF$_3$, CH$_3$, C$_2$H$_5$, C$_3$H$_7$, straight and branched alkyl chain up to six carbons, straight and branched alkoxy/sulphoxy chain up to six carbons, phenyl or and substituted phenyl ring, wherein the substituents in phenyl ring are selected from the group consisting of F, Cl, Br, NO$_2$, CF$_3$, CH$_3$, C$_2$H$_5$, C$_3$H$_7$, straight and branched alkyl chain up to six carbons, with a compound selected from a the group consisting of acetophenone, p-methyl acetophenone, 3,4,5-trimethoxy acetophenone, p-trilluoromethyl acetophenone, m-methyl acetophenone, 4-methoxyphenyl acetophenone, 3-methylthio acetophenone, 4-chlorophenyl acetophenone, 2-chlorophenyl acetophenone, N-(4-acetylphenyl)acetamide, 1-(4-(diethylamino)phenyl)ethanone, 3,4-dimethoxyphenyl acetophenone, 3-fluorophenyl acetophenone, 3-bromophenyl acetophenone, 2-nitro acetophenone, and 4-hydroxy acetophenone (in 1:1 to 1:1.5 ratio) in presence of an acid or mild Lewis acid under neat reaction conditions or optionally in presence of an organic solvent at a temperature ranging between 40° C. to 120° C. for a period ranging between 1 to 7 hrs to give respective chalcone of the formula (III) wherein R is selected form the group consisting of H, CHO, COCH$_3$, NHCOCH$_3$, F, Cl, Br, NO$_2$, CF$_3$, OCF$_3$, CH$_3$, C$_2$H$_5$, C$_3$H$_7$, straight and branched alkyl chain up to six carbons, straight or and branched alkoxy/sulphoxy chain up to six carbons, phenyl and substituted phenyl ring, wherein the substituents in phenyl ring are selected from the group consisting of F, Cl, Br, NO$_2$, CF$_3$, CH$_3$, C$_2$H$_3$, C$_3$H$_7$,straight and branched alkyl chain up to six carbons and R$^2$, R$^3$, R$^4$ which may be unsubstituted or substituted by one, two or three substituents being independently selected from the group of consisting of F, Cl, Br, NO$_2$, CF$_3$, CH$_3$, C$_2$H$_5$, OCH$_3$, OC$_2$H$_5$, CF$_3$, NMe$_2$, NEt$_2$, SCH$_3$, and HCOCH3

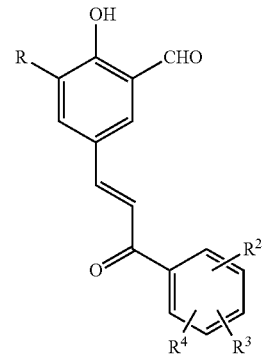

Formula III

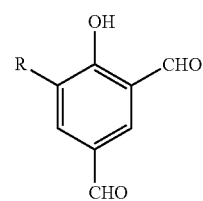

Formula I (ii) reacting a compound of the formula (III), with an active methylene compound selected from the group consisting of diethylmalonate and dimethylmalonate, in 1:1 to 1:1.2 ratio, in an organic solvent in presence of a base at a temperature in the range between 40° C. to 120° C. for a period ranging between 1 to 8 hrs;

(iii) removing excess solvent under reduced pressure to obtain a residue;

(iv) neutralizing the residue with an acid to a pH of 6.5-8.0;

(v) adding water to the residue to form a mixture;

(vi) extracting the mixture with a water immiscible solvent selected from a the group consisting of chloroform, dichloromethane, ethyl acetate, and diethyl ether;

(v) removing the solvent to dryness under reduced pressure, and purifying the product by chromatographic methods to furnish the compound of the formula (IV), wherein R is selected form a the group consisting of H, CHO, COCH$_3$, NHCOCH$_3$, F, Cl, Br, NO$_2$, CF$_3$, OCF$_3$, CH$_3$, C$_2$H$_5$, C$_3$H$_7$, straight or branched alkyl chain up to six carbons, straight or and branched alkoxy/sulphoxy chain up to six carbons, phenyl or and substituted phenyl ring, wherein the substituents in phenyl ring are selected from the group consisting of F, Cl, Br, NO$_2$, CF$_3$, CH$_3$, C$_2$H$_5$, C$_3$H$_7$, straight and branched alkyl chain up to six carbons and R$^2$, R$^3$, R$^4$ which may be unsubtituted or substituted by one, two or three substituents being independently selected from the group consisting of F, Cl, Br, NO$_2$, CF$_3$, CH$_3$, C$_2$H$_5$, OC$_2$H$_5$, CF$_3$, NMe$_2$, NEt$_2$, SCH$_3$, and NHCOCH$_3$,

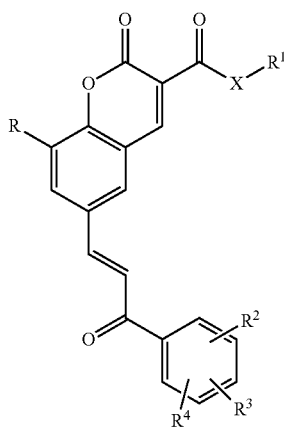

Formula IV (vii) adding aqueous KOH or NaOH, with concentration ranging between 10% to 50%, to a solution of the compound of the formula (IV) in EtOH or MeOH and stirring the mixture vigorously for a period of between 1-4 hrs at a temperature between 15° C.-50° C.;

(viii) removing the solvents to obtain a second residue;

(ix) acidifying the residue with dilute HCl;

(x) adding water to the acidified residue;

(xi) removing precipitates which provides a crude product of the formula (V), wherein R is selected from the group consisting of H, CHO, COCH, NHCOCH, F, Cl, Br, NO$_2$, CF$_3$, OCF3, CH$_3$, C$_2$H$_5$, C$_3$H$_7$, straight and branched alkyl chain up to six carbons, straight and branched alkoxy/sulphoxy chain up to six carbons, phenyl and substituted phenyl ring, wherein the substituents in the phenyl ring are selected from the group consisting of F, Cl, Br, NO$_2$, CF$_3$, CH$_3$, C$_2$H$_5$, C$_3$H$_7$, straight and branched alkyl chain up to six carbons and R$^2$, R$^3$, R$^4$ which may be unsubtituted or substituted by one, two or three substituents being independently selected from the group consisting of F, Cl, Br, NO$_2$, CF$_3$, CH$_3$, C$_2$H$_5$, OCH$_3$, OC$_2$H$_5$, CF$_3$, NMe$_2$, NEt$_2$, SCH$_3$, and NHCOCH$_3$,

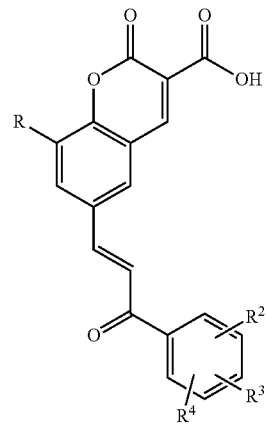

Formula V (xii) adding thionyl chloride to the compound of the formula (V), in 2:1 to 2.5:1 ratio, in an organic solvent selected from the group consisting of DCM, CCl$_4$, benzene, and toluene;

(xiii) refluxing for a period ranging between 1-6 hrs;

(xiv) evaporating the resulting solution to dryness under reduced pressure to obtain a third residue, (xv) dispersing the third residue in an organic solvent selected from the group consisting of DCM, CCl4, benzene, and toluene;

(xvi) evaporating the solvent under reduced pressure to obtain a fourth residue; and (xvii) dissolving the fourth residue in a solvent selected from the group consisting of DCM, CCl$_4$, benzene, and Toluene and to obtain a solution, (xviii) adding an amine to the above solution obtained in step (xvii), in 1:1 to 1:1.5 ratio, with stirring and allowing to react at a temperature ranging between 15° C.-50° C. for a period ranging between 5-60 min;

(xix) dry the solution obtained in step (xviii under reduced pressure to obtain the compound of formula (VII).

9. The process as claimed in claim 8, wherein the acid used in steps (i) and (iv) is selected from the group consisting of dilute HCl, dilute H$_2$SO$_4$, and glacial acetic acid.

10. The process as claimed in claim 8, wherein the organic solvent used in steps (i) and (ii) is selected from the group consisting of dioxane, ethanol, THF, and benzene.

11. The process as claimed in claim 8, wherein the base used in step (ii) is selected from the group consisting of pyridine, N-methyl morpholine, and piperidine.

12. The process as claimed in claim 8, wherein the amine used in step (xvi) is selected from the group consisting of ethylamine, methylamine, N,N-diethylamine, N,N-dimethylamine, and propylamine.

13. The process of claim 8, further comprising the step of purifying the compound of formula (VII).

\* \* \* \* \*